(12) United States Patent
Morgan, Jr. et al.

(10) Patent No.: US 7,416,728 B2
(45) Date of Patent: *Aug. 26, 2008

(54) GROWTH BLOCKING AGENTS

(75) Inventors: A. Charles Morgan, Jr., Edmonds, WA (US); Edward V. Quadros, Brooklyn, NY (US); Sheldon P. Rothenberg, New York, NY (US)

(73) Assignees: Kyto Biopharma, Inc., Palm Beach Gardens, FL (US); State University of New York, Brooklyn, NY (US)

( * ) Notice: Subject to any disclaimer, the term of this patent is extended or adjusted under 35 U.S.C. 154(b) by 460 days.

This patent is subject to a terminal disclaimer.

(21) Appl. No.: 10/956,735

(22) Filed: Oct. 1, 2004

(65) Prior Publication Data

US 2005/0169910 A1 Aug. 4, 2005

Related U.S. Application Data

(63) Continuation of application No. 09/654,116, filed on Aug. 30, 2000, now abandoned, which is a continuation of application No. 08/584,959, filed on Jan. 11, 1996, now abandoned, which is a continuation-in-part of application No. 08/476,440, filed on Jun. 7, 1995, now abandoned, which is a continuation-in-part of application No. 08/381,522, filed on Jan. 31, 1995, now abandoned, which is a continuation-in-part of application No. 08/306,504, filed on Sep. 13, 1994, now Pat. No. 5,688,504, which is a continuation-in-part of application No. 07/880,540, filed on May 8, 1992, now abandoned.

(51) Int. Cl.
*A61K 39/00* (2006.01)
*C07K 16/00* (2006.01)

(52) U.S. Cl. .................. 424/141.1; 530/388.1

(58) Field of Classification Search .............. 530/388.1; 424/141.1
See application file for complete search history.

(56) References Cited

U.S. PATENT DOCUMENTS 5,688,504 A 11/1997 Morgan, Jr. .............. 424/141.1

FOREIGN PATENT DOCUMENTS

| WO | WO 81/02930 | 10/1981 |
| WO | WO 90/10014 | 9/1990 |
| WO | WO 93/23557 | 11/1993 |
| WO | WO 96/08515 | 3/1996 |

OTHER PUBLICATIONS

Amagasaki et al, Expression of Transcobalamin II receptors by human leukemia K562 and HL-60 cells, 1990, Blood, vol. 76, p. 1380-6.*

Kroes et al, Enhanced therapeutic effect of methotrexate in experimental rat leukemia after inactivation of cobalamin (vitamin B12) by nitrous oxide, 1986, Cancer Chemother Pharmacol, vol. 17, p. 114-20.*

Bose et al., "In Vitro and in Vivo Inactivation of Transcobalamin II Receptor by its Antiserum," *J. Biological Chemistry* 271(8):4195-4200, Feb. 23, 1996.

Burch, "Mass Ligand Binding Screening for Receptor Antagonists: Prototype New Drugs and Blind Alleys," *J. of Receptor Research* 11(1-4):101-113, 1991.

Carmel and Linker-Israeli "Monoclonal Antibodies to Different Sites on Human Transcobalamin II," *Proc. Soc. Exp. Biol. Med.* 188(1):77-81, May 1988.

Dialog database, Abstract of JP 63-003262, Jan. 8, 1988.

Hall et al., "Cyclic Activity of the Receptors of Cobalamin Bound to Transcobalamin II," *J. Cell. Physiol.* 133(1):187-191, Oct. 1987.

Herbert, "Staging Vitamin B-12 (Cobalamin) Status in Vegetarians," *Am. J. Clin. Nutr.* 59(Suppl.):1213S-1222S, May 1994.

Kuntz, "Structure-Based Stategies for Drug Design and Discovery," *Science* 257:1078-1082, Aug. 21, 1992.

Marcoullis, G. et al., "Blocking and Binding Type Antibodies against All Major Vitamin $B_{12}$-Binders in a Pernicious Anaemia Serum," *British Journal of Haematology* 43: 15-26, 1979.

McLean et al., "Antibodies to Transcobalamin II Block in Vitro Proliferation of Leukemic Cells," *Blood* 89(1):1-8, Jan. 1, 1997.

Moestrup et al., "Megalin-Mediated Endocytosis of Transcobalamin-Vitamin-$B_{12}$ Complexes Suggests a Role of the Receptor in Vitamin-$B_{12}$ Homeostasis," *P.N.A.S. USA* 93:8612-8617, Aug. 1996.

Ostray and Gams, "Cellular Fluxes of Vitamin $B_{12}$," *Blood* 50(5):877-88, Nov. 1977.

Platica et al., "The cDNA Sequence and the Deduced Amino Acid Sequence of Human Transcobalamin II Show Homology with Rat Intrinsic Factor and Human Transcobalamin I," *J. Biol. Chem.* 266(12):7860-7863 Apr. 25, 1991.

Quadros et al., "Characterization of the Human Placental Membrane Receptor for Transcobalamin II-Cobalamin," *Arch. Biochem. Biophys.* 308(1):192-199. Jan. 1994.

Quandros et al., "Endothelial Cells from Human Umbilical Vein Secrete Functional Transcobalamin II," *Am. J. of Physiology* 256(Cell Physiol. 25):C296-C303, 1989.

Quadros, E.V. et al., "Epitope Specific Monoclonal Antibodies (mAbs) to Human Transcobalamin II (TCII) can Induce Apoptosis By Inhibiting the Cellular Uptake of Cabalamin (Cbl)," *Blood* 86(10 Suppl. 1): 125A, 1995.

(Continued)

*Primary Examiner*—Mark Navarro
(74) *Attorney, Agent, or Firm*—Seed IP Law Group PLLC

(57) ABSTRACT

There is disclosed anti-receptor and growth blocking agents to the vitamin $B_{12}$/transcobalamin II receptor and binding sites. The anti-receptor and growth blocking agents antagonize or modulate the vitamin $B_{12}$/transcobalamin II receptor or binding sites, causing cellular depletion of vitamin $B_{12}$, thus inhibiting cell division or causing apoptosis. Anti-receptor and growth blocking agents of the present invention include proteins (such as antibodies and antibody derivatives), peptides and small organic molecules. In a preferred embodiment, the anti-receptor agent is an antibody to the vitamin $B_{12}$/transcobalamin II receptor.

5 Claims, 8 Drawing Sheets

OTHER PUBLICATIONS

Ramasamy et al., "Effect of Lectins on the Cobalamin-protein Binding Reactions: Implications for the Tissue Uptake of Cobalamin," *J. Nutr. Biochem. 1*:213-219, Apr. 1990.

Rudinger, *Peptide Hormones*, Parsons (ed.), University Park Press, Baltimore, Chapter 1, "Characteristics of the Amino Acids as Components of a Peptide Hormone Sequence," pp. 1-7.

Shimizu, N. et al., "Experimental Study of Antitumor Effect of Methyl-$B_{12}$," *Oncology 44*: 169-173, 1987.

Webster's II New Riverside University Dictionary, Houghton Mifflin Company, 1994, New York, p. 812.

White et al., "Combinations of Anti-Transferrin Receptor Monoclonal Antibodies Inhibit Human Tumor Cell Growth in Vitro and in Vivo: Evidence for Synergistic Antiproliferative Effects," *Cancer Res. 50*(19):6295-6301, Oct. 1, 1990.

Youngdahl-Turner et al., "Binding and Uptake of Transcobalamin II by Human Fibroblasts," *J. Clin. Invest. 61*(1):133-141, Jan. 1978.

\* cited by examiner

Vitamin B12 Receptor Modulation

GROWTH BLOCKING AGENTS

CROSS-REFERENCE TO RELATED APPLICATIONS

This application is a continuation of U.S. patent application Ser. No. 09/654,116, filed Aug. 30, 2000, which is a continuation of U.S. patent application Ser. No. 08/584,959, filed Jan. 11, 1996, now abandoned, which is a continuation-in-part of U.S. patent application Ser. No. 08/476,440, filed Jun. 7, 1995, now abandoned, which is a continuation-in-part of U.S. patent application Ser. No. 08/381,522, filed Jan. 31, 1995, now abandoned, which is a continuation-in-part of U.S. patent application Ser. No. 08/306,504, filed Sep. 13, 1994, now issued as U.S. Pat. No. 5,688,504, which is a continuation-in-part of U.S. patent application Ser. No. 07/880,540 filed May 8, 1992, now abandoned, all of which applications are incorporated herein by reference in their entireties.

TECHNICAL FIELD

The present invention generally relates to anti-receptor or growth blocking agents directed to vitamin $B_{12}$/transcobalamin II receptors or binding sites, and more specifically, to agents which can cause the cellular depletion of vitamin $B_{12}$ by antagonizing or modulating the vitamin $B_{12}$/transcobalamin II receptors or binding sites, thereby inhibiting cell division and/or resulting in apoptosis.

BACKGROUND OF THE INVENTION

As has been demonstrated in experimental in vitro data, pre-clinical animal models, and patient studies, vitamin $B_{12}$ is a co-enzyme necessary in cell division, as well as cellular metabolism, in proliferating normal and neoplastic cells. Insufficient vitamin $B_{12}$ causes cellular division to be held in abeyance and ultimately may result in apoptosis. The nutrient is generally derived from dietary intake and is transported throughout the body complexed to transport proteins. The complex of transport protein and vitamin $B_{12}$ is recognized by a cellular receptor which internalizes the complex and releases the vitamin intracellularly. The overall process has been reviewed in *GUT* 31:59, 1991. Vitamin $B_{12}$ is taken in through the diet. Binding proteins in the saliva (R-binder) and gut (intrinsic factor-(IF)) complex vitamin $B_{12}$ after release from endogenous binding proteins by action of enzymes and low pH in the stomach. Vitamin $B_{12}$ is transferred across the intestinal epithelium in a receptor specific fashion to transcobalamin II (TcII). The vitamin $B_{12}$/transcobalamin II complex is then transported throughout the body and recognized by receptors present on dividing cells, internalized and released within the cell where it is utilized by certain enzymes as a co-factor.

The high affinity receptor in dividing tissues or cells responsible for internalization of vitamin $B_{12}$ recognizes transcobalamin II complexed with vitamin $B_{12}$. The vitamin $B_{12}$/TcII receptor recognizes only the vitamin $B_{12}$/TcII complex and not the serum transport protein or the vitamin alone. The receptor is down-regulated on non-dividing cells; the mechanism for supplying non-dividing cells with vitamin $B_{12}$ is poorly understood. However, it is known that more vitamin $B_{12}$ is required during cell division than during metabolism, and that the vitamin $B_{12}$/TcII receptor is the only high affinity means for cellular uptake of vitamin $B_{12}$ during cell division. When stimulated to divide, cells demonstrate a five to ten fold increase in transient expression of this receptor leading to vitamin $B_{12}$ uptake which precedes actual DNA synthesis (*J. Lab. Clin. Med.* 103:70, 1984). Vitamin $B_{12}$ receptor levels may be measured by binding of $^{57}$Co-vitamin $B_{12}$ complexed to transcobalamin II (present in serum) on replicate cultures grown in chemically defined medium without serum. No receptor mediated uptake occurs in the absence of carrier protein.

Dividing cells, induced to differentiate, lose receptor expression and no longer take up vitamin $B_{12}$. More importantly, leukemic cells, deprived of vitamin $B_{12}$, will stop dividing and die (*Acta Haemat.* 81:61, 1989). In a typical experiment, leukemic cell cultures were deprived of serum for 3 days, and then supplemented either with serum (a source of vitamin $B_{12}$) or a non-metabolizable analogue of vitamin $B_{12}$ and cultured up to five days. Cell cultures supplemented with vitamin $B_{12}$ continued to grow, whereas those deprived of the active nutrient stopped growing and die.

Based on these observations, it has been suggested that whole body deprivation of vitamin $B_{12}$ may be useful in the treatment of cancer or other disorders characterized by uncontrolled growth of cells. Moreover, because of the critical role played by vitamin $B_{12}$-containing enzymes in cell division, it is believed that vitamin $B_{12}$ deprivation may be used in combination with chemotherapeutic drugs which inhibit cellular replication. For example, when vitamin $B_{12}$ depletion was combined with methotrexate, the two modalities together were more efficient in depleting folate levels in leukemic cells than either alone (*FASEB J.* 4:1450, 1990; *Arch. Biochem. Biophys.* 270:729, 1989; *Leukemia Research* 15:165, 1991). Folates are precursors in the production of DNA and proteins. In typical experiments, cultures of leukemic cells were exposed to nitrous oxide for several hours to convert the active form of endogenous vitamin $B_{12}$ to an inactive form. Replicate cultures were then left without further treatment, or additionally treated with methotrexate. Cellular folate levels were measured three days later. Cells treated with the combination (i.e., both methotrexate and inactive vitamin $B_{12}$) showed a more striking decrease in cellular folate levels than with either of the two approaches alone. This combination also results in a higher cell kill in vitro. When this approach was applied to the treatment of highly aggressive leukemia/lymphoma in animal models (*Am. J. Haematol.* 34:128, 1990; *Anticancer Res.* 6:737, 1986; *Cancer Chemother. Pharmacol.* 17:114, 1986; *Br. J. Cancer* 50:793, 1984), additive or synergy of anti-tumor action was observed, resulting in prolonged remissions and cures. The following Table 1 summarizes the observed additive or synergistic results:

TABLE 1

Vitamin $B_{12}$ Depletion (Nitrous Oxide) in Combination Therapy

| Study | Drugs Used in Combination with Vitamin $B_{12}$ Depletion | Therapeutic Results |
| --- | --- | --- |
| Myelocytic leukemia/rats | cycloleucine | additive |
|  | 5-FU | additive |
|  | methotrexate | synergistic |
| Acute leukemia/rats | 5-FU | additive |
| Acute leukemia/rats | methotrexate | synergistic |
| Acute leukemia/rats | cycloleucine | synergistic |

A key finding in the experiments described above was that short-term (hours to days), whole body depletion of vitamin $B_{12}$ can act synergistically with chemotherapeutic drugs (such as methotrexate and 5-FU) to inhibit tumor growth and treat animals with leukemia/lymphoma. Despite synergistic antitumor activity, there was no toxicity attributable to the short-term vitamin $B_{12}$ depletion for proliferating normal cells. This combination therapy was demonstrated in multiple animal models. Observations in patients have indicated that long-term (months to years) vitamin $B_{12}$ depletion is required to produce significant normal tissue toxicity. Even in those cases, subsequent infusion of vitamin $B_{12}$ can readily reverse symptomology (*Br. J. Cancer* 5:810, 1989).

Because of the promise of this therapeutic approach, various methods have been sought to efficiently and controllably perform a temporary depletion of vitamin $B_{12}$. Such methods, however, affect all of the body's stores of vitamin $B_{12}$. They include dietary restriction, high doses of vitamin $B_{12}$ analogues (non-metabolizable-competitive antagonists which act as enzyme inhibitors), and nitrous oxide (transformation of vitamin $B_{12}$ to inactive form). These different methods have been used in culture systems and in animals to deplete vitamin $B_{12}$. The most efficient and the most utilized method has been the inhalation of nitrous oxide (laughing gas). Animals are maintained typically under an atmosphere of 50% to 70% of nitrous oxide for periods from a few hours to a few days, causing the conversion of endogenous vitamin $B_{12}$ into an inactive form. This methodology has been utilized in combination with drugs for therapy of leukemia/lymphoma. A further method for vitamin $B_{12}$ depletion involves infusion of a non-metabolizable analogue of vitamin $B_{12}$ which essentially dilutes out the active form. This form of therapy is not specific for dividing cells but affects liver dependent metabolic processes. Another approach includes restricting the dietary intake of vitamin $B_{12}$. This method, however, requires very long periods of dietary restriction and is offset by hepatic storage of vitamin $B_{12}$. All of these methods suffer from problems of specificity, since they affect both vitamin $B_{12}$-dependent growth as well as basal metabolism, and therefore are not particularly suited to the development of anti-proliferative pharmaceutical products.

Accordingly, there is a need in the art for agents which will cause the cellular depletion of vitamin $B_{12}$, and which selectively affect dividing cells. The present invention fulfills this need, and provides further related advantages.

SUMMARY OF THE INVENTION

The present invention discloses anti-receptor and growth blocking agents which antagonize or modulate the vitamin $B_{12}$/transcobalamin II receptor ("$B_{12}$/TcII receptor") or binding sites on the $B_{12}$/TcII complex ("binding site"). Such agents cause cellular depletion of vitamin $B_{12}$ by interfering with a cell surface receptor or a binding site, thus inhibiting cell division and, ultimately, may cause apoptosis. Anti-receptor or growth blocking agents which antagonize (e.g., block) $B_{12}$/TcII receptor or binding site function, competitively binding to a $B_{12}$/TcII receptor or a binding site thereby inhibiting cellular uptake of vitamin $B_{12}$. Alternatively, such antagonists may sterically hinder recognition of the $B_{12}$/TcII complex by $B_{12}$/TcII receptor or interfere with a binding site by binding sufficiently near a $B_{12}$/TcII receptor or a binding site to inhibit cellular uptake of vitamin $B_{12}$.

Anti-receptor or growth blocking agents of the present invention which modulate a $B_{12}$/TcII receptor or a binding site, may bind to a $B_{12}$/TcII receptor or a binding site and cause the removal or clearing of the receptor for a period of time, and thus inhibit cellular uptake of vitamin $B_{12}$. Anti-receptor or growth blocking agents of the present invention include proteins (e.g., antibodies and antibody derivatives), peptides, and small organic molecules that can antagonize or modulate the $B_{12}$/TcII receptor or a binding site and cause the cellular depletion of vitamin $B_{12}$, thereby inhibiting cell division of normal or hyperproliferative cells.

In one embodiment of the present invention, an anti-receptor agent to the $B_{12}$/TcII receptor is disclosed. This agent is capable of competitively antagonizing or modulating the receptor to inhibit cellular uptake of vitamin $B_{12}$. In a preferred embodiment, the anti-receptor agent is an antibody (or derivative thereof) to the $B_{12}$/TcII receptor.

In another embodiment of the present invention, a growth blocking agent directed to the vitamin $B_{12}$ binding site on TcII is disclosed. (FIG. 4, type 1). A growth blocking agent of this embodiment affects vitamin $B_{12}$ uptake, since vitamin $B_{12}$ cannot enter the cell in effective amounts without binding to TcII.

In another embodiment of the present invention, a growth blocking agent directed to a receptor binding site on holo-TcII is disclosed. (FIG. 4, type 2). A growth blocking agent of this embodiment affects vitamin $B_{12}$ uptake by inhibiting the $B_{12}$/TcII complex from binding to a $B_{12}$/TcII receptor.

In another embodiment of the present invention, a growth blocking agent directed to a binding site on apo-TcII (other than the vitamin B12 binding site on TcII), is disclosed. (FIG. 4, type 1). The growth blocking agent of this embodiment affects vitamin $B_{12}$ uptake by inhibiting the binding of $B_{12}$/TcII complex to a $B_{12}$/TcII receptor and/or inhibiting the binding between vitamin $B_{12}$ and TcII.

In another embodiment of the present invention, a growth blocking agent directed to clearing sites is disclosed. A growth blocking agent of this embodiment is capable of redirecting TcII or the $B_{12}$/TcII complex to the reticulo-endothelial organs, such as the liver and spleen, thus inhibiting vitamin $B_{12}$ cellular uptake.

In another aspect, the present invention discloses a method for inhibiting cell division in warm-blooded animals or biological preparations by administering to the animal an anti-receptor agent or a growth blocking agent, wherein the agent is capable of antagonizing or modulating the receptor or binding site to inhibit cellular uptake of vitamin $B_{12}$ for the treatment of neoplastic disorders and other disorders characterized by uncontrolled cell growth.

In yet another aspect of the present invention, a method is disclosed for inhibiting cellular uptake of vitamin $B_{12}$ in a warm-blooded animal or a biological preparation by administering to the animal an anti-receptor agent or a growth blocking agent, wherein the agent is capable of antagonizing or modulating the receptor or binding site.

These and other aspects of the present invention will become evident upon reference to the following detailed description and attached drawings. In addition, various references are set forth which describe in more detail certain procedures and/or compositions, and are hereby incorporated by reference in their entirety.

DETAILED DESCRIPTION OF THE INVENTION

Figure 1:
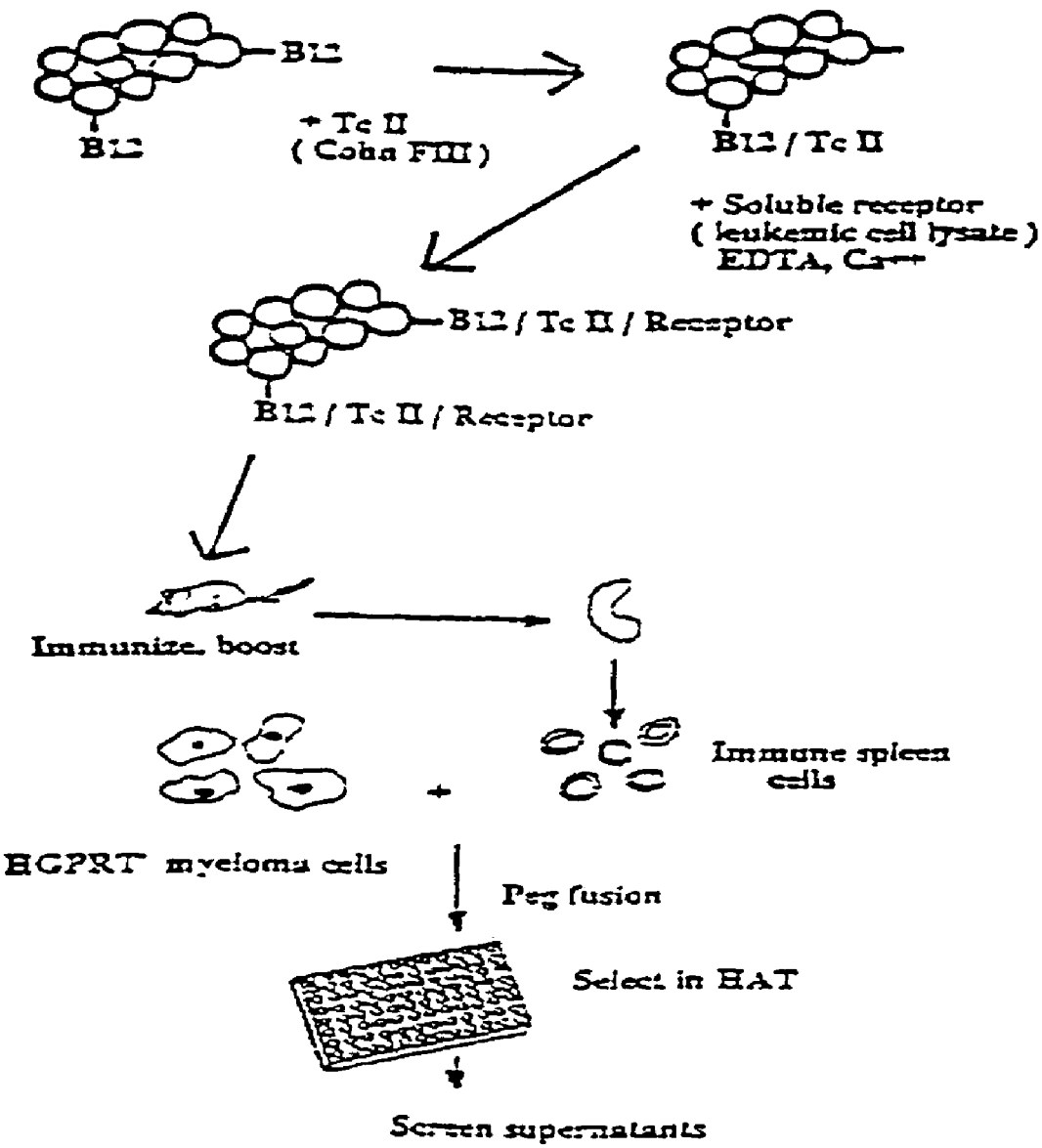
FIG. 1 is a schematic which illustrates the development of $B_{12}$/TcII receptor antibodies through the production of murine monoclonal antibodies to the receptor using immunogens consisting of a solid phase, affinity sorbent for the receptor to elicit antibodies, followed by hybridoma generation and screening using both binding and functional assays.

The present invention discloses anti-receptor agents to the vitamin $B_{12}$/transcobalamin II receptor ("$B_{12}$/TcII receptor") and growth blocking agents to binding sites on the vitamin $B_{12}$/transcobalamin II complex ("$B_{12}$/TcII complex") and TcII. Within the context of the present invention, "anti-receptor agents" or "growth blocking agents" cause cellular depletion of vitamin $B_{12}$, by acting as competitive antagonists or as modulating agents to $B_{12}$/TcII receptors or binding sites on the $B_{12}$/TcII complex or TcII. Anti-receptor and growth blocking agents of the present invention recognize certain functional and nonfunctional binding sites on TcII and $B_{12}$/TcII complex and $B_{12}$/TcII cell surface receptors, as described below, and inhibit vitamin $B_{12}$ uptake by the cell. Since dividing cells require larger quantities of vitamin $B_{12}$, this results in the inhibition of cellular proliferation and, under certain conditions, may result in apoptosis.

In one aspect of the present invention, anti-receptor agents and growth blocking agents may be competitive antagonists or modulating agents. Competitive antagonists are agents which competitively bind to (or sterically hinder) a $B_{12}$/TcII receptor or a binding site, thereby inhibiting cellular uptake of vitamin $B_{12}$. Modulating agents are agents which bind to a $B_{12}$/TcII receptor or a binding site, and result in the clearing or removal of a $B_{12}$/TcII receptor or a $B_{12}$/TcII complex for a period of time (generally hours). Once a modulating agent is no longer present, the vitamin $B_{12}$ levels are re-established.

In another aspect, the present invention is directed to novel methods for depletion of cellular vitamin $B_{12}$ in warm-blooded animals or biological preparations by administration of an anti-receptor or growth blocking agent, for example, administering to a warm-blooded animal an anti-receptor or growth blocking antibody, wherein the antibody competitively antagonizes or modulates the $B_{12}$/TcII receptor or binding site to inhibit cellular uptake of vitamin $B_{12}$. Due to the low expression of $B_{12}$/TcII receptors (e.g., only a few thousand per cell) and the need to generate functional antibodies that elicit a biological response (e.g., cause cellular depletion of vitamin $B_{12}$ and, perhaps, apoptosis), methods of immunization are described herein for eliciting functional antibodies (e.g., combining affinity enrichment of the receptor together with the use of solid phase immunogens to enhance the response to these weakly immunogenic and poorly expressed antigens). Only a portion of these anti-receptor antibodies function as antagonists or to modulate cellular receptors or binding sites. Appropriate antibodies may be identified by bioassays as illustrated below and in FIG. 1.

In the context of the present invention, the term "anti-receptor agent" or "growth blocking agent" refers to compounds or compositions such as proteins, peptides, and small organic compounds which act by binding to binding sites on $B_{12}$/TcII complex or TcII, in the case of growth blocking agents, or the cell surface $B_{12}$/TcII receptors, in the case of anti-receptor agents, and inhibit vitamin $B_{12}$ uptake, resulting in the cellular depletion of vitamin $B_{12}$.

The term "binding site" refers to a functional or nonfunctional binding site on TcII or the $B_{12}$/TcII complex which, when bound by an agent of the present invention, results in occlusion, causes conformational changes which would occlude, or otherwise hinders, ie., sterically, or modulates the functional binding site on TcII or the $B_{12}$/TcII complex such that vitamin $B_{12}$ uptake is inhibited. In the context of this invention, binding site is not intended to refer to the $B_{12}$/TcII receptor.

Figure 4:
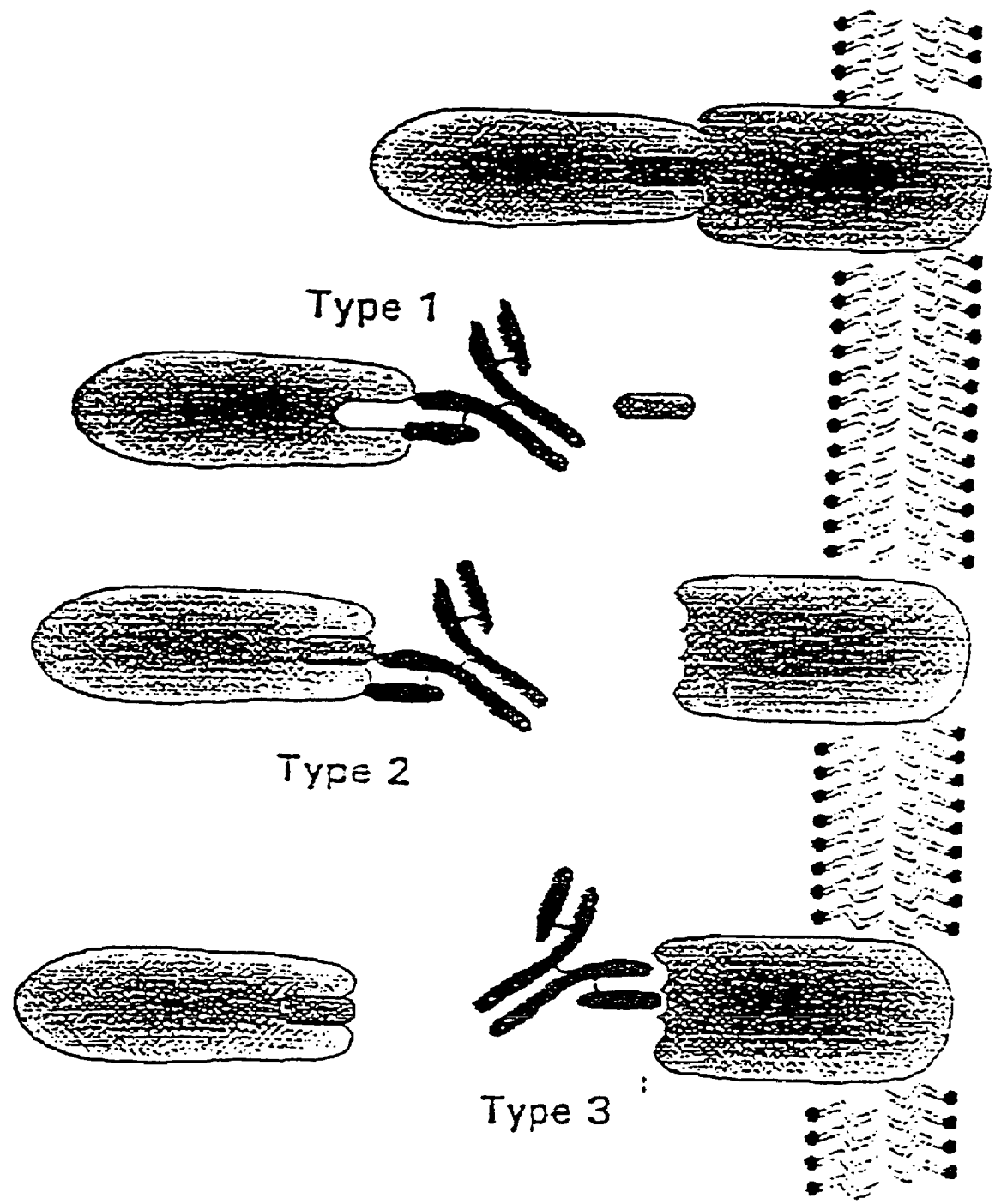
FIG. 4 illustrates some of the binding types utilized in the present invention.

The term "$B_{12}$ binding site on TcII," specifically refers to a binding site on TcII which governs binding between TcII and vitamin $B_{12}$ (FIG. 4, type 1). A growth blocking agent of this binding site affects vitamin $B_{12}$ uptake by inhibiting vitamin $B_{12}$ uptake.

The term "receptor binding site on holo-TcII" specifically refers to a binding site on the TcII/vitamin $B_{12}$ complex which allows the complex to bind to a cell surface $B_{12}$/TcII receptor (FIG. 4, type 2). A growth blocking agent of this binding site affects vitamin $B_{12}$ uptake by inhibiting the complex from binding to a $B_{12}$/TcII receptor.

The term "binding site on apo-TcII" (FIG. 4, type 1) specifically refers to a binding site on TcII, before binding to the vitamin $B_{12}$. A growth blocking agent of this binding site affects vitamin $B_{12}$ uptake by inhibiting the $B_{12}$/TcII complex from binding a $B_{12}$/TcII receptor and/or inhibiting vitamin $B_{12}$ from binding TcII.

The term "clearing sites" refers to any binding sites on TcII or the $B_{12}$/TcII complex to which a growth blocking agent is capable of binding. A growth blocking agent for this binding site is capable of redirecting TcII or the $B_{12}$/TcII complex to a reticulo-endothelial organ, such as the liver or spleen, thus affecting vitamin $B_{12}$ uptake.

The term "$B_{12}$/TcII receptor" refers to a cell surface receptor for a $B_{12}$/TcII complex. (FIG. 4, type 3). An anti-receptor agent for this receptor affects vitamin $B_{12}$ uptake by inhibiting vitamin $B_{12}$ uptake into the cell.

The term "biological preparation" refers to any animal cell or tissue ex vivo. Suitable preparations include, by way of example, HepG2 cells, COS cells, 293 cells, K562 cells, and ATT20 cells.

The term "apoptosis" refers to cell death. The term "inhibiting" refers to a decrease or prevention of the ability to perform the particular function which is deemed inhibited. For example, with relation to vitamin $B_{12}$ uptake, the term generally refers to greater than about a 50 percent decrease in vitamin $B_{12}$ uptake, and preferably, greater than about a 90% decrease in vitamin $B_{12}$ uptake.

In one aspect of the present invention, anti-binding or growth blocking agents are antibodies. In the context of the present invention, the term "antibody" includes both monoclonal and polyclonal antibodies and further includes an intact molecule, a fragment thereof, or a functional equivalent thereof.

Anti-receptor and growth blocking antibodies of the present invention fall into several functional and specificity categories and have different pharmaceutical applications. Suitable anti-receptor antibodies to the $B_{12}$/TcII receptor include those which (1) bind but do not produce a biological response; (2) cross-link, modulate and clear the surface of receptors and, if the concentration of modulating antibody is maintained in the patient's circulation at sufficient levels, modulate any newly synthesized receptor when it is re-expressed (IgM antibodies typically are the most efficient modulating agents); and (3) function as competitive antagonists for vitamin $B_{12}$ binding. Each of these types of antibodies may be distinguished by specific binding or functional assays in a series of screens, beginning with primary screens using initial hybridoma cultures, through secondary screens of clones, and finally to more labor intensive assays of final, stably secreting clones. (See Examples 1, 2, 8-12 and FIG. 1.)

Suitable growth blocking antibodies include any antibody which is capable of binding to, or otherwise occluding, a binding site or any antibody which is capable of binding to a binding site and clearing TcII or $B_{12}$/TcII complex from circulation. For example, a suitable growth blocking antibody to a chosen binding site may be selected by any one of several means known in the art, including the use of functional binding assays described in detail in Sambrook et al., *Antibodies: A Laboratory Manual*, Cold Spring Harbor Laboratory, 1989, and the Examples below. Briefly, antibodies are incubated with a pre-formed complex of ($^{57}$Co) Vitamin $B_{12}$/Tcll then exposed to a suitable vitamin $B_{12}$ receptor bearing cells including, by way of example, K562 cells (ATCC accession no. CCL-243). Uptake is then measured using any suitable means of detecting the radiolabeled antibodies (see, Example 10).

In a preferred embodiment, murine antibodies are generated and may be screened by comparison of nitrous oxide conversion of vitamin $B_{12}$ and antiproliferative effects of antibody-mediated depletion of tumor cells in a biological preparation. The pharmaceutical application of murine antibodies is limited by the potential for anti-murine antiglobulin responses in patients (i.e., immunogenicity). Thus, murine antibodies require genetic manipulation for their conversion to human-mouse chimeras. Numerous methods exist for conversion of murine antibodies to chimeras in which the heavy and light chain constant regions are substituted with human versions or in which all but the CDRs (complementary determining regions) are substituted with their human equivalents. (See *Biochem. J.* 281:317, 1992; *Proc. Nat. Acad. Sci. USA* 86:10029, 1989; *Methods Enzymol.* 178:515, 1989; *Cancer Res.* 51:181, 1991; *Biotechniques* 7:360, 1989; *J. Immunol.* 143:3589, 1989; *Int. J. Cancer* 44:424, 1989; *Proc. Nat. Acad. Sci. USA* 86:3833, 1989).

In another preferred embodiment of the present invention, the serum half-life of a growth blocking or an anti-receptor agent is adjusted for the particular application. For certain applications it may be valuable to increase the serum half-life using any one of several means, including selecting heavy chain constant regions which will impart long serum half-life. Particularly when using a competitive antagonist, the affinity and the length of exposure to target cells may be of critical importance to efficacy. Optimal cell depletion is accomplished by blocking $B_{12}$/TcII receptors or binding sites for several hours to several days. Suitable antibodies may be selected by any one of several means including radiolabelling IgG, injecting it into a warm-blooded animal, drawing blood samples over a period of time, and ascertaining the level of IgG. Chimeric IgG antibodies need to be assessed for this property individually. Antibodies with longer half-lives may be the most suited to applications where receptor antagonism or modulation must be maintained for prolonged periods. (See *Biochem. J.* 281:317, 1992; *Proc. Nat. Acad. Sci. USA* 86:10029, 1989; *Methods Enzymol.* 178:515, 1989; *Cancer Res.* 51:181, 1991; *Biotechniques* 7:360, 1989; *J. Immunol.* 143:3589, 1989; *Int. J. Cancer* 44:424, 1989; *Proc. Nat. Acad. Sci. USA* 86:3833, 1989). A longer serum half-life may be engineered using only one of several means, including selecting for IgG4 and IgG2, human IgM heavy chains or screening multiple IgG heavy chain allotypes for these longest half-life using any one of several means.

Completely human monoclonal antibodies can also be created by in vitro immunization procedures, employing the specific sorbents used in murine hybridoma generation. (See Example 1 below and FIG. 1.) Furthermore, a variety of techniques exist for in vitro immunization and human antibody generation (*J. Immunol. Methods* 145:71, 1991; *Hybridoma* 9:81, 1990; *Proc. Nat. Acad. Sci. USA* 85:3995, 1988; *Immunol. Lett.* 17:29, 1988; *BBRC* 148:941, 1987; *Immunol. Lett.* 16:75, 1987; *Tissue Antigens* 30:25, 1987). See also U.S. Pat. No. 4,879,225.

In another aspect of the present invention, genetic engineering techniques can be used to produce various antibody derivatives, including fragments, peptides, organic molecules and mimetics, as well as a variety of antibodies modified with regard to affinity or effector function. All these various antibody derivatives can be produced from an antibody to a $B_{12}$/TcII receptor or a binding site. Essentially, one can consider such an antibody as containing, within its antigen combining site, the information necessary to combine with its target and elicit a biologic response. This information can be put into the context of molecules of different size and different forms, and are collectively referred to herein as "antibody derivatives". Preferably, murine antibodies are used.

The aforementioned chimeric antibodies (which are typically whole IgG) can be engineered by a number of different approaches but essentially seek to replace murine constant regions with those of human origin. Alternatively, the CDRs (the specific regions interacting with the antigen) can be isolated from the antigen combining site and then engrafted into a framework of human variable and constant regions. This latter type of antibody should be less immunogenic than chimeric antibodies in which only constant regions are replaced. More recently, efforts have been initiated in identifying the most probable residues within a murine antibody structure that elicits antiglobulin or HAMA responses. Essentially, these may be hydrophilic residues that are in contact with solvent and can be identified and replaced by mutagenesis of antibody genes.

For certain applications it may be favorable to shorten serum half-life in order to provide better penetration into tissues or to clear background blood levels. Such applications include bone marrow protection from chemotherapeutic drugs or radiation. In this case, it may be appropriate to adjust the biological half-life of the antibody to induce a short term anti-proliferative block of bone marrow stem cells, timed to coincide with administration of chemotherapeutic drugs or radiation. Following cessation of treatment with the toxic therapy, cell proliferation would be restored as the growth blocking or anti-receptor agent was eliminated from the body.

In yet another aspect of the present invention, a whole antibody is engineered into one of the various fragments as identified in Table 2. The most common antibody fragments produced by genetic engineering are the Fab or Fv fragments.

Fab fragments can be created by enzymatic digestion of whole IgG, but this usually entails a significant loss in product, as well as inconsistencies in the final antibody form. Thus, genetically engineered Fab is believed to be a more consistent product, and can be produced in gram-per-liter quantities in bacterial expression systems. An important step in producing such engineered fragments is to isolate the regions of the antibody involved in antigen binding (i.e., the CDRs) and place them within the context of human framework. Essentially, Fv is created in a similar manner to Fab, except that the Ch1 and Vh domains are not cloned along with CDR regions. This gives rise to a smaller fragment that requires peptide linkers to join the heavy and light chain components. Moreover, it is believed that certain heavy chain domains can combine with target antigens without the participation of a light chain domain. This is likely to be confined to rather primitive antibodies and antigen-binding specificities. The smallest antibody fragment consists of peptides derived from the information in the CDR, but retain the ability to bind to target structures. Since the affinity of these antibody fragments (as well as Fab and Fv) must be maintained with cloning, bivalent antibody fragments may be created, as well as ones in which mutagenesis and selection has been applied to select a higher affinity version. Preferably, antibody affinity to its target is in the range of about $10^{-7}$ to $10^{-10}$ M, and, even more preferably, affinity is greater than $10^{-9}$ M.

TABLE 2

Genetically Engineered, Antibody Derivatives Which May Function As Receptor or Binding Site Antagonists

| Derivative | References |
|---|---|
| Antibody Fragments | |
| CH$_2$ deletion | Mueller et al., PNAS 87: 5702-5, 1990; Kashmiri, 3rd IBC Conference on Antibody Engineering, May 14, 1992 |
| CH$_3$ deletion | Kashmiri, 3rd IBC Conference on Antibody Engineering, May 14, 1992 |
| Fab | Ward et al., Nature 341: 544-6, 1989; Chiswell & McCafferty, TIBTech 10: 80-84, 1992; Carter et al., Biotechnology 10: 163-167, 1988; Better et al., Science 240: 1041-43, 1988 |
| Fv | Huston et al., Methods in Enzymology 203: 46-88, 1991; Colcher et al., JNCI 82: 1191-97, 1990; Skerra & Pluckthun, Science 240: 10-38, 1988; Whitlow & Filpula, Methods: A Companion to Methods in Enzymology 2: 97-105, 1991 |
| Heavy chain domain | Ward et al., Nature 341: 484-5, 1989 |
| MRU/Peptide mimetics | Williams et al., PNAS 86: 5537-41, 1989; Taub et al., J. Biol. Chem. 264: 259-65, 1989 |
| Chimeric Antibodies | |
| Chimeric (mouse V region/ human constant regions) | R. F. Kelley, 3rd IBC Conference on Antibody Engineering, May 14, 1992; Morrison & Oi, Adv. Immunol. 44: 65-92, 1989; Larrick & Fry, Hybridoma 2: 172-89, 1991 |
| Primatized (mouse V region/ primate constant regions) | R. A. Newman, 3rd IBC Conference on Antibody Engineering, May 14, 1992 |
| CDR grafted (mouse CDR, human constant and framework regions) | Chiswell & McCafferty, TIBTech 10: 80-84, 1992; T. Rees, 3rd IBC Conference on Antibody Engineering, May 14, 1992; C. Queen, 3rd IBC Conference on Antibody Engineering, May 14, 1992; Junghans et al., Cancer Res. 50: 1495-1502, 1990; Tempest et al., Biotechnology 9: 266-71, 1991; Jones et al., Nature 321: 522-5, 1986 |
| Hydrophillic residue substitution | T. Rees, 3rd IBC Conference on Antibody Engineering, May 14, 1992 |
| Modified Antibodies | |
| Antigen Affinity | Ashkenazi et al., PNAS 87: 7150-4, 1990; Clarkson et al., Nature 352: 624-628, 1991; Queen et al., PNAS 86: 10029-33, 1989; Tempest et al., Bio/Technology 9: 266-72, 1991; Chiswell & McCafferty, TIBTech 10: 80-84, 1992; Foote & Winter, J. Mol. Biol. 224: 487-99, 1992 |
| Effector Functions | Wawrzynczak et al., Mol. Immunol. 29: 213-20, 1992; Wawrzynczak et al., Mol Immunol. 29: 221-7, 1992; Lund et al., J. Immunol. 147: 2657-62, 1991; Duncan et al., Nature 332: 563-4, 1988; Duncan & Winter, Nature 332: 738-40, 1988 |
| Bi-specific | Berg et al., PNAS 88: 4723-7, 1991; D. Segal, Chem. Immunol. 47: 179-213, 1989; Rodriques et al., Int. J. Cancer Sup. 7: 1-6, 1992 |
| Di-/multi-meric | Pack & Pluckthun, Biochem. 31: 1579-84, 1992; H. V. Raff, 3rd IBC Conference on Antibody Engineering, May 14, 1992; M. Whitlow, 3rd IBC Conference on Antibody Engineering, May 14, 1992; Carter et al., Bio/Immunol. 149: 120-6, 1992 |
| Organic molecule mimetics (peptiomimetic) | Satagovi et al., Science 253: 792-5, 1991; Wolf, 3rd IBC Conference on Antibody Engineering, May 14, 1992 |
| Immunoadhesions | Marstets et al., J. Biol. Chem. 267: 5747-50, 1992; Chatnow, et al., Int. J. Cancer (Suppl.) 7: 69-72, 1992 |
| Anti-idiotypic antibody | Escobar et al., Viral Immunology 5: 71-79, 1992 |

In another embodiment of the present invention, an anti-receptor or a growth blocking agent's affinity is increased using any one of several means. Retaining high affinity of an antigen-combining site for its target structure is important for a receptor antagonist since its effectiveness is determined by its binding affinity (in combination with half-life). Numerous techniques have been developed that allow one to increase affinity 2-3 fold (and sometimes up to 5-fold) over native antibody including, by way of example, cloning antibodies onto an IgM constant region along with joining segments for production of pentavalent antibodies capable of binding multiple binding sites on multiple molecules. (See Table 2.)

In some circumstances, modification of effector functions, either enhancing or decreasing complement-activating ability, or the ability to interact with effector cells would be advantageous. Such circumstances include, by way of example, if the antibody was used to remove TcII from incubation. Effector functions of a whole antibody used as an anti-receptor antagonist or a growth blocking antagonist may degrade the selectivity of an antagonist and give more potential for toxicity. Modification of effector function may be determined by any one of several techniques including, by way of example, assays for Fcr mediated binding described in Harel et al., *Cancer Res.* 50:6311-5315, 1990; Woodhouse, -C. S. and A. C. Morgan, Jr., *Cancer Res.* 49:2766-2772, 1989.

In another embodiment of the present invention, monovalent fragments are engineered into di- or multi-valent constructs to improve binding affinity. Several post-translational techniques which allow for non-covalent association of monomeric antibody derivatives into di- or multi-meric forms can be used to enhance affinity. (See Table 2.) Multimeric or dimeric forms of antibody fragments may provide advantages from the standpoint of affinity or effector function. Multimeric or dimeric molecules may be also more efficient in modulating receptors from surfaces. (See Table 2.)

As discussed in greater detail below, small molecule receptor antagonists are believed to be more useful for certain medical applications due to their low cost, their utility in oral administration and ease of manufacturing. In addition to peptide structures derived from antibodies known as molecular recognition units ("MRU"), molecular modeling techniques can be used to create organic molecule mimetics from antibodies using peptide mimetic intermediaries. (see Table 2).

Isolation and cloning of the $B_{12}$/TcII receptor would allow the creation of a soluble receptor as a competitor. However, such receptor forms may have a short serum half-life, and poor bioavailability. One way to increase the half-life and bio-availability of these cloned receptors is to attach them by recombinant techniques to immunoglobulin-constant regions. This provides for the longer serum half-life and potential effector functions that may be useful in activity of the receptor antagonist. Such combinations of receptor and immunoglobulin heavy and light chain constant region genes is termed an immunoadhesion.

Using the information present in the combining site of a functional antibody to the $B_{12}$/TcII receptor, a second antibody recognizing the combining site of the first can be generated (termed an anti-idiotypic antibody). Such an antibody is the mirror image of the first and thereby an analogue to the receptor itself. Thus, it can be utilized in a manner similar to that of immunoadhesion.

An important step in generating the antibody derivatives discussed above is the isolation of the genes encoding the complementary determining regions (CDR) of an antibody to a $B_{12}$/TcII receptor. This can be accomplished by any one of a number of techniques. For example, one suitable technique involves immunization of mice, hybridoma formation, and selection to isolate a murine antibody of appropriate specificity. Once murine antibodies are produced, their CDR can be isolated and employed in one of the antibody derivatives identified in Table 2. To elicit such an antibody, the immunogen strategy outlined in Example 1 may be utilized. A similar immunogen approach can be employed in an in vitro immunization scheme where antibodies specific for the $B_{12}$/TcII receptor can be elicited and then immortalized through EBV infection, electrofusion or hybrid-hybridoma formation. Alternatively, the genes can be isolated through PCR amplification and then cloned into one of the antibody derivatives previously mentioned.

Human antibodies may be generated using mice that are transgenic for human immunoglobulin genes. This is accomplished genetically by inserting human IgG genes into the germ line of mice (N. Lonberg, *First Annual Meeting on Commercializing Human Monoclonal Antibodies*, Dec. 17-18, 1992). Alternatively, severe combined immunodeficient (SCID) mice have been transplanted with human leukocytes which will proliferate in the mouse and be available for immunization. (Duchosal et al., *Nature* 355:258-262, 1992). In this case, the antibody specific for the $B_{12}$/TcII receptor or binding sites can be isolated after immunization of the human leukocytes, with an immunogen which enhances the frequency of elicitation of specific antibodies (as described in Example 1 below). Alternatively, antibodies of the appropriate specificity may be generated from combinatorial libraries of germ line IgG genes. In such a process, libraries of Fab fragments, for example, are screened for binding to antigens of the appropriate specificity (essentially equivalent to an un-immunized B-cell repertoire). The same libraries can be created from an immunized repertoire, thus increasing the opportunity for identifying an appropriate antibody. Moreover, the probability of identifying an antibody of appropriate specificity and/or affinity using this technique would be enhanced if prior immunization is carried out following the techniques disclosed in Example 1 below.

Vitamin $B_{12}$ should be used to overcome any antiproliferative effect of the antibodies on the B-cells from which they originated. Briefly, the antiproliferative effect is a result of the fact that all eukaryotic sources of TcII have considerable amino acid homology due to the common functions of vitamin $B_{12}$ and receptor binding. However, different species of TcII can be discriminated immunologically. Although polyclonal antibodies in rabbits generally are cross-reactive and are capable of binding both human and mouse TcII, mouse monoclonal antibodies generated to human TcII are not capable of binding both. This indicates that the hybridomas which are cross-reactive are not elicited or not able to expand after elicitation.

Any antiproliferative effect can be overcome by administering high doses of vitamin $B_{12}$ which, through passive diffusion, can enter cells without TcII. Any suitable form of vitamin $B_{12}$ known in the art may be used for supplementation. Briefly, B-cells may be cultured in or the animal vehicle administered vitamin $B_{12}$, (preferably, in the form of hydroxycobalamin which can bind to serum protein non-specifically) during antibody production.

In another embodiment of the present invention, a growth blocking or anti-receptor agent is a small organic compound or peptide. Despite the potential utility of antibodies and antibody derivatives as receptor antagonists, there may be pharmaceutical applications for which they are not appropriate due to their cost, potential for immunogenicity, or need for specialized forms of delivery such as orthotopic or oral administration. For these purposes, small organic compounds or peptides may be more suitable. Such peptides and compounds may be isolated by: (1) screening of bacterial peptide expression libraries, antibody paratope analogs or antibody Fab expression libraries to identify peptide or antibody variable region inhibitors (*Gene* 73:305, 1988; *Proc. Nat. Acad. Sci. USA* 87:6378, 1990; *BioChromatography* 5:22, 1990; *Protein Engineering* 3:641, 1989); (2) rational drug design programs using antibodies as a "pharmacophore" to create organic molecule analogs (*Biotechnology*, Jan. 19, 1991), or traditional rational drug design programs using crystallized vitamin receptor to identify peptide or organic inhibitors (*Biochem. J.* 268:249, 1990; *Science* 248:1544, 1990); and (3) screening a library of organic molecules, as present in fermentation broths of microorganisms, for inhibition of vitamin $B_{12}$ uptake, identifying the biochemical nature of inhibitory compound(s), and chemically synthesizing analogs to explore structure-function relationship and to identify potent inhibitor(s).

Small organic compounds and peptide receptor antagonists for the $B_{12}$/TcII receptor or binding sites may be identified through the use of an appropriate assay. In one embodiment, this assay entails tracking the uptake of radiolabeled vitamin $B_{12}$, complexed with its carrier protein, transcobalamin II. (See Examples 1 and 2 below.) Other assays can also prove useful, including specific binding assays using antibodies which act as competitive antagonists. Through these means a repertoire of protein and non-protein molecules suitable for human use can be generated, and may be used to define optimal regimens to manipulate vitamin $B_{12}$ uptake and bioavailability for different pharmaceutical applications that require an alteration in cellular proliferation.

In one aspect of the present invention, a growth blocking agent is directed to a $B_{12}$ binding site on TcII. (FIG. 4, type 1). Growth blocking agents inhibit vitamin $B_{12}$ uptake by binding the B12 binding site on TcII inhibiting binding between vitamin $B_{12}$ and TcII. This affects vitamin $B_{12}$ uptake, since vitamin $B_{12}$ cannot enter the cell in effective amounts without binding to TcII. A suitable growth blocking agent is selected using the techniques as described above, and in Examples 8-12. Such antibodies include, by way of examples, 2-2, 3-11, and 4-7 (see FIGS. 5, 6, and 7).

In another aspect of the present invention, a growth blocking agent is directed to a receptor binding site on holo-TcII. A growth blocking agent bound to this site will affect vitamin $B_{12}$ uptake by inhibiting the complex from binding to the cell surface receptor. A suitable growth blocking agent is selected as described in detail above and in Examples 8-12. Such antibodies include, by way of examples 2-2, 3-11, and 4-7.

Figure 5:
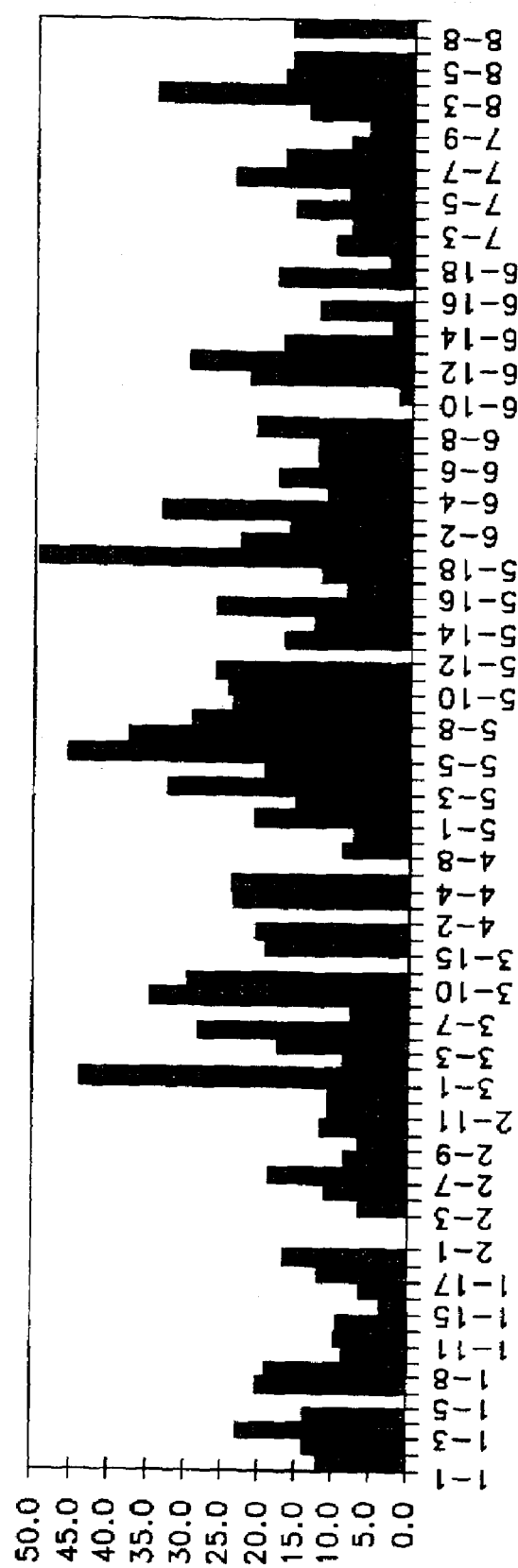
FIG. 5 illustrates the screening assay used to identify monoclonal antibodies that recognize human TcII and inhibit binding of vitamin $B_{12}$.
Figure 6:
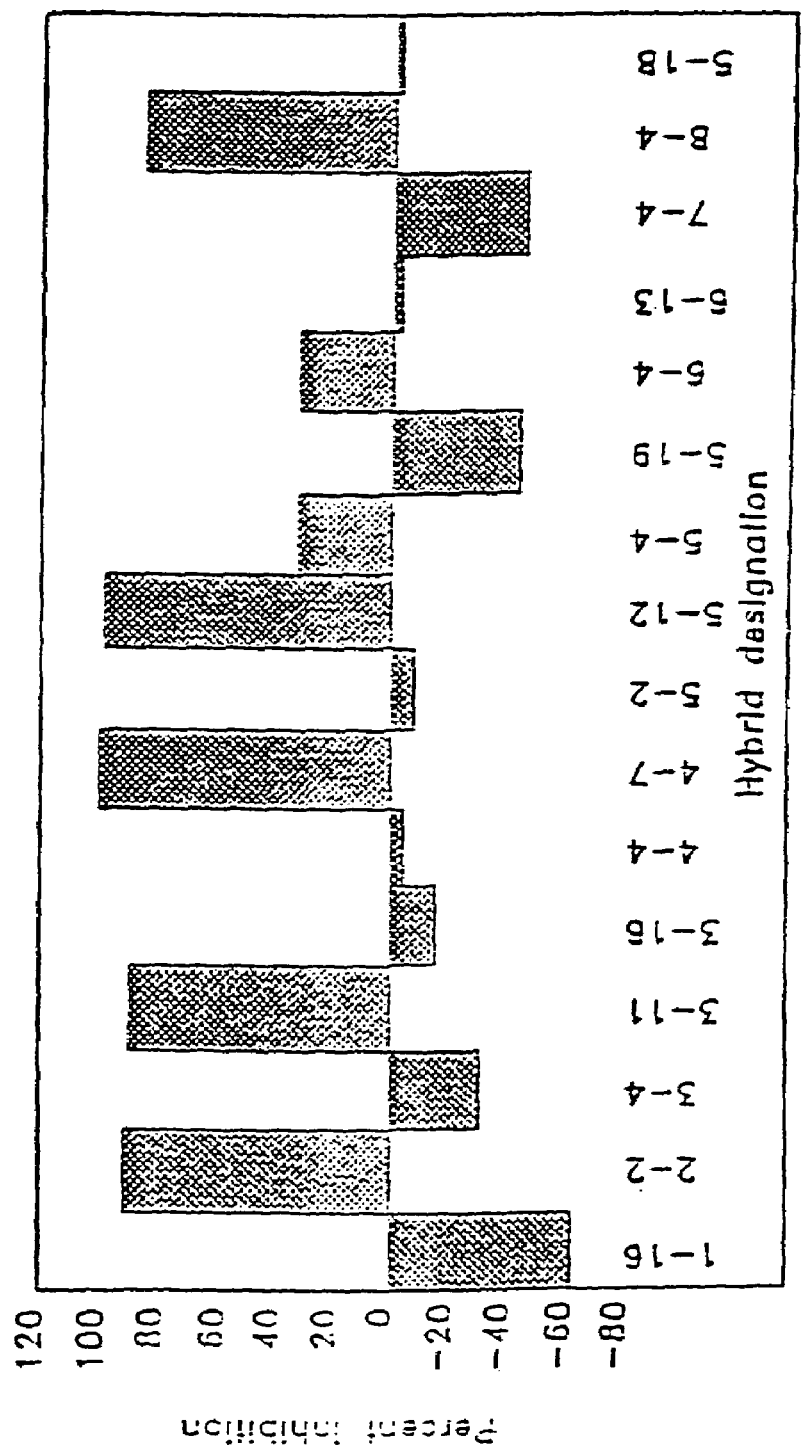
FIG. 6 illustrates screening of monoclonal antibodies for abilities ability to inhibit uptake of $^{57}Co$ labelled vitamin $B_{12}$.

In another aspect of the present invention, a growth blocking agent is directed to a binding site on apo-TcII. A growth blocking agent bound to this site will affect vitamin $B_{12}$ uptake by inhibiting a $B_{12}$/TcII complex from binding a $B_{12}$/TcII receptor and/or inhibiting binding between TcII and vitamin $B_{12}$. A suitable growth blocking agent is selected as described in detail above and in Examples 8-12. Such antibodies include, by way of examples 1-18, 5-19, and 7-4 (FIG. 5).

In another aspect of the present invention, a growth blocking agent is directed to any binding sites on TcII or a $B_{12}$/TcII complex which a growth blocking agent is capable of binding. A growth blocking agent bound to this site is capable of redirecting TcII or the $B_{12}$/TcII complex to the reticulo-endothelial organs, such as the liver and spleen, thus affecting vitamin $B_{12}$ uptake. Sequestration of $B_{12}$/TcII complex into the liver serves two roles: first, the removal of available vitamin $B_{12}$ from peripheral tissues, circulating cells and neoplastic disease found therein and second, the provision of vitamin $B_{12}$ for hepatic function after lysosomal release following endocytosis.

In this aspect of a growth blocking antibody, their Fc regions are optimal for interactions with reticulo-endothelial elements. This may be either a property of a given antibody or one achieved by re-engineering. This may include selection of IgM, IgG1, or IgG3 isotypes for a re-engineered antibody or chemical modification to enhance RES removal. For example, in the latter case, conjugation of ligands for the asialoglycoprotein receptor to antibody. Such growth blocking agents are capable of removing 90% of injected material into the liver.

In a particularly preferred method of isolating a growth blocking agent, recombinant human TcII, produced by any one of several suitable means, including, by way of example, that described in Example 8, is utilized to elicit antibodies using any one of several techniques described above. Hybridomas are then screened to identify those which recognize recombinant human TcII using any one of several suitable techniques, including by way of example, enzyme linked immunoassay (ELISA). Antibodies which recognize TcII (growth blocking agents) are then tested for the presence of one of the above-described binding sites, using any one of several techniques including, by way of example, radioimmunoassay (RIA). Growth blocking agents may be evaluated for specificity for either holo- or apo-TcII using any one of several techniques, including immunoprecipitation techniques as described in Example 11. Growth blocking agents may be tested for their ability to inhibit uptake of vitamin $B_{12}$ in a biological preparation using any one of several suitable means, including, by way of example, a cellular uptake assay as described in Example 10. Suitable selected growth blocking agents may then be purified using any one of several suitable techniques, including ELISA sandwich assays and those described in Examples 12-14. Preferably, suitable growth blocking agents have an affinity in the range of about $10^{-7}$ to $10^{-10}$ and, even more preferably, the agents have an affinity greater than $10^{-9}$.

In another aspect of the present invention, an anti-receptor agent is directed to a $B_{12}$/TcII receptor, these agents bind to a $B_{12}$/TcII receptor itself and inhibit contact with the TcII or the $B_{12}$/TcII complex. Because growth blocking agents described above recognize the CDR, they have an inherent advantage over the anti-receptor agents. The $B_{12}$/TcII receptor is expressed at extremely low levels on the cell surface. As a result, antibodies to the receptor have not previously been derived and the receptor has not been purified, sequenced or cloned.

In yet another aspect of the present invention, anti-receptor or growth blocking agents are antibodies and are administered to treat either a biological preparation or a warm blooded animal. In one treatment aspect of the present invention, the manner in which the antibody-based products of the present invention are used is dependent on the mechanism of action of anti-receptor or growth blocking agents and their serum half-life. In one embodiment, an anti-receptor or a growth blocking antibody acts as an antagonist of the binding of the $B_{12}$/TcII complex in a typical mass action fashion. The goal for patient administration is to achieve and maintain serum concentrations of the antibody at a level sufficient to block $\geq 50\%$, and more preferably $\geq 90\%$ or all of the uptake of vitamin $B_{12}$ into target cells for a prescribed period of time, typically 1 to 7 days. The duration of the blockade is determined by the target cell and the biologic response to be elicited (e.g., cell death or cessation of cell division).

The degree of inhibition of vitamin $B_{12}$ uptake can be determined by any one of a number of means. If the target cell is one that is easily accessible (e.g., lymphocytes or bone marrow or biological preparation), then samples from patients can be assessed for residual vitamin $B_{12}$ uptake at various periods following antibody administration. Alternatively, patient samples can be assessed for binding with FITC conjugated anti-receptor or growth blocking antibody using flow cytometry. If it is difficult to acquire patient samples (as in the treatment of solid tumors), an indirect assessment of receptor blockade may be performed by measuring serum levels of antibody using specific immunoassays (e.g., the use of individually specific anti-idiotypic antiglobulin to measure circulating levels of vitamin $B_{12}$ receptor antibody or other assays as disclosed below) and referring to amounts of antibody required to maintain receptor blockade in vitro.

Figure 2:
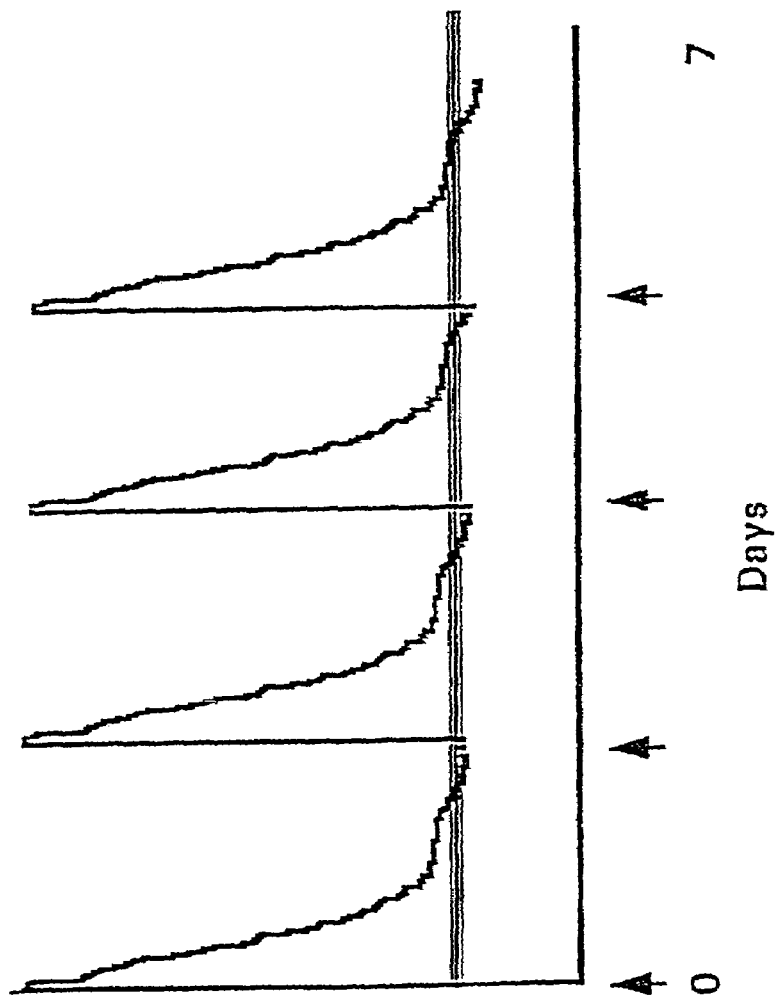
FIG. 2 illustrates the administration of vitamin $B_{12}$ anti-receptor antibodies (i.e., infusions every 2 to 3 days) to maintain serum concentrations above the requisite level (indicated by tri-partite line) for complete or near complete receptor blockade. The requisite concentration is determined by the amount of antibody required to block ≦90% of vitamin $B_{12}$ uptake into cultured leukemic cells (K562) as assessed by functional assays.

The amount of anti-receptor or growth blocking antibody and timing of administration may also be determined using in vitro testing followed by in vivo studies. Primarily, the method used includes measuring serum concentrations, as illustrated in FIG. 2. For example, antibody administered in a dose range of 1 to 500 mg is quantitated in serum by solid phase, competition ELISA using biotinylated anti-receptor antibody binding to a solid-phase receptor source (e.g., glycoprotein isolate from detergent extract of K562 leukemic cells). Unlabeled antibody is used as a competitor to develop a standard curve. As shown in FIG. 2, the serum half-life of an immune complex of IgG antibody is 24 hours, requiring dosing approximately every 36 to 48 hours to maintain serum concentrations above that required for maximal blockade (shown by tri-partite line). The longer the inherent serum half-life of the anti-receptor antibody, the fewer administrations required. Thus, an immune complex of IgM antibody with a half-life of several days may be more advantageous under certain circumstances. By way of example, plasma concentration of TcII is 30 picograms/mL or 96 micrograms for the entire body, there is about 10% holo-TcII. The steady state synthesis allows for replacement of 80 µg of $B_{12}$/TcII complex every 24 hours. Assuming a 10-fold antibody to the binding site and an antibody half life of 48 hours, then the warm-blooded animal would only require 2 mg/48 hours. Quadros and Rothenberg, *Am. J. Physio.*, 256:296-303, 1989.

Agents capable of modulating or "capping" vitamin $B_{12}$ receptors may be used in a manner similar to competitive antagonists. However, knowledge of the parameters of receptor or binding site modulation is necessary to optimize therapy. Modulation, capping, patching, clustering, or immobilization can be the result of interactions of antibodies with cell surface antigens, receptors, or binding sites. The terms describe a range of responses from complete clearance of antigen from the surface to an inhibition of antigen mobility within the membrane. Whatever type of interaction occurs, antibody binding can result in a loss of function or triggering of a biological response, depending on the nature of the antigen. There have been a variety of antigens, receptors, and binding sites demonstrated to undergo modulation when bound by antibody, but there appears to be little relationship between antigen number and the ability to be modulated (*Acta Haemotol.* 73:196, 1985). Since bivalency (or multivalency) is required to cross-link antigen and cause modulation, the ability to do so is governed by antigen density and distribution, as well as the distance spanned by antibody (e.g., an IgM can span a greater distance than IgG). In addition, accessory antigens, antibodies or cells can also enhance modulation. For instance, modulation of receptors is enhanced by the presence of complement, by HIV gp120 protein for CD-4 on T-cells, and by monocytes for CD-5 modulation on T-cells (*J. Immunol.* 133:2270, 1984; *Science* 245:1380, 1989; *J. Immunol.* 144:239, 1990).

Essential for modulation is the epitope on the target antigen, recognized by antibody. *J. Immunol.* 137:2286, 1986. In the case of cell surface IgD immunoglobulin on B-cells, antibodies modulate according to the portion of the cell surface IgD molecule bound. *J. Immunol.* 139:2873, 1987. Once modulated, antigen or receptor can have several fates: immobilization or clustering on the cell surface, internalization and degradation or shedding. The degree of modulation may vary significantly even with the same antibody, antigen, and target cell population. *Acta Haematol.* 76:119, 1986. Whichever fate, biological responses may be suppressed or triggered by modulation and not be re-established for periods of 24 to 72 hours, coincident with antigen or receptor re-expression.

Selectivity may be achieved in modulation also. Most types of cells can be modulated by antibodies as described for fibroblasts (*J. Cell Sci.* 98:191, 1991), adipocytes (*Int. J. Immunopharmacol.* 6:193, 1984), pancreatic islet cells (*Diabetologia* 24:117, 1983), sperm (*Exp. Cell Res.* 144:275, 1983), glomerular epithelium (*J. Immunol.* 135:2409, 1985) and tumor cells (*Int. J. Cancer* 448:1095, 1989). However, modulation is most readily achieved on lymphoid cells. Depending on the tissue location, such lymphocytes may be more or less susceptible to modulation. For instance, antibody to OKT-3 like antigens on guinea pig T-cells were susceptible to modulation when present in all lymphoid tissues except thymus. *J. Immunol.* 138:2500, 1987. CD-5 antigen or human T-cells can be modulated on peripheral cells without modulation of T-cells in lymph nodes by controlling the dose of antibody. The reverse can also be achieved by injecting a modulating dose of T101 (anti-CD-5) for peripheral cells, and following with a subsequent second infusion of T101 which is delivered selectively to lymph node T-cells (*J. Immunol.* 133: 1641, 1984; *N. Eng. J. Med.* 315:673, 1986). Modulation is not restricted to just antibodies; small compounds and peptides can also cause redistribution of a receptor (*J. Biol. Chem.* 167:3530, 1992).

Common to many non-neoplastic disease processes is a stage in which the disease process itself, or its symptoms, can be halted or ameliorated by the use of an anti-proliferative agent such as vitamin $B_{12}$ receptor or binding site antagonists. These commonly recognized stages include a sensitization or elicitation phase in which immune cells responsible for the disease become turned on by antigen specific or non-specific means, followed by a proliferative phase in which the immune cells expand in number, and finally a symptomatic phase in which the expanded immune cells create tissue damage directly or indirectly. Because of this, anti-proliferative chemotherapeutic drugs are commonly utilized in the treatment of many diseases other than cancer, but are limited in use to life threatening situations due to their associated toxicity. Anti-proliferative agents, such as the ones of the present invention (with little of the direct toxicity of chemotherapeutic drugs), may be used more widely. More specifically, the anti-receptor and growth blocking agents of the present invention are not destructive to plasma membrane processes (e.g., ion transport). In addition, the anti-proliferative activity is reversible by administration of vitamin $B_{12}$. Furthermore, the agents of this invention may not be mutagenic, teratogenic, or carcinogenic since they act at the level of the plasma membrane, and not at the level of the nucleus, and DNA by intercalation or cross-linking (as many chemotherapeutic drugs act).

Anti-receptor or growth blocking agents are employed to create a transient state of TcII deficiency. This transient deficiency results in an inhibition of uptake of the $B_{12}$/TcII complex onto the cellular receptor, cellular depletion of vitamin $B_{12}$ and, ultimately, may result in death to tumor cells. Depending on the type of neoplastic disorder and the tumor burden, the duration of the transient deficiency may be optimally varied from one to six weeks (see Example 4). TcII is rapidly synthesized. Thus, cessation of antibody treatment will result in reinstitution of normal $B_{12}$/TcII levels. Alternatively, patients may be treated with vitamin $B_{12}$ or folate to reverse the effects of the antibody treatment.

An understanding of the pharmaceutical applications for the compounds of the present invention requires a knowledge of the cell types targeted by such therapy. To this end, various pharmaceutical applications are disclosed in Table 3 below.

TABLE 3

Target Cells for Antagonists

| Target Cell | Other Proliferation Associated Markers | Potential Pharmaceutical Applications |
|---|---|---|
| Activated T-Cell | IL-2 receptor Transferrin Receptor Insulin Receptor Class II Histocompatibility Antigens | Graft versus Host Disease Organ Transplants Auto-Immune Diseases Asthma Crohn's Disease |
| Tumor Cells | Tumor Assoc. Ags. Ki67 Transferrin Receptor | Tumor Therapy (alone and in combination with chemotherapeutic drugs) |
| Bone Marrow Stem Cells | CD-34 Transferrin Receptor Class II Histocompatibility Antigens IL-1, IL-3 Receptors | Allogeneic Bone Marrow Transplants Reduction in Toxicity of Chemotherapy |
| Proliferating Fibroblasts | Thy 1.1 Transferrin Receptor Insulin & Insulin-like Growth-Factor Receptors Fibroblast Growth-Factor Receptor | Inhibition of Adhesions, Scarring Scleroderma |
| Proliferating Epithelium or Epidermal (Keratinocytes) | EGF Receptor Proto-Oncogenes | Psorasis |

Proliferating and activated T-cells can cause a wide variety of diseases ranging from the chronic inflammation of Crohn's disease to more acute organ graft rejection. In all of these diseases, the T-cell may serve a central pathogenic role or a more accessory role. Anti-proliferative chemotherapeutic drugs serve to reduce symptomotology and in some cases lead to long-term remission. Similarly, proliferating fibroblasts and epithelial cells may give rise to diseases characterized by cell overgrowth. Anti-receptor and growth blocking agents may be used to replace or used in combination with existing chemotherapeutic regimens in these diseases. An important aspect of the use of anti-proliferative anti-receptor and growth blocking agents in these diseases is not to apply it so aggressively or with improper timing such that normal healing (adhesions, scarring) or cell renewal (psoriasis) processes are also inhibited. As such, low doses of anti-receptor or growth blocking agents may be used during healing and higher doses once healing is completed. Alternatively, anti-receptor or growth blocking agents may not be administered at all until after healing is completed. The agents can be administered to patients for prolonged periods of time (i.e., months) in the adjuvant setting, in order to check proliferation of any hyperproliferative or neoplastic cells that have not been killed by the prior treatments by vitamin $B_{12}$ depletion, as described in detail below.

As previously mentioned, anti-receptor or growth blocking agents can be used to deprive neoplastic cells of vitamin $B_{12}$. It has already been shown that sufficient deprivation leads to the apoptosis of rapidly proliferating lymphoid neoplasm such as leukemia and lymphoma. Moreover, short term treatment to reduce cellular availability of this nutrient, combined with existing chemotherapeutic agents, markedly improve therapeutic efficacy.

For solid tumors, vitamin $B_{12}$ depletion may induce cytostasis and differentiation as well as apoptosis. Thus, anti-receptor or growth blocking agents may be used to induce differentiation in hormonally responsive solid tumors. An increase in the number of cells expressing a differentiated phenotype should translate into an increase in expression of hormone receptors. The hormone receptor status of tumors, such as breast and prostrate cancer, are directly correlated with their response to hormonal therapy. Accordingly, anti-receptor or growth blocking agents can be used to increase the number of receptor positive tumor cells or increase receptor density in order to enhance efficacy of subsequent hormonal therapy.

Anti-receptor or growth blocking agents may affect both replicating normal and neoplastic cells. However, bone marrow progenitors demonstrate differential sensitivity or response. Thus, anti-receptor or growth blocking agents can be used to modulate sensitivity of bone marrow progenitors so as to enhance their resistance to the toxic effects of chemotherapeutic agents. Such chemotherapeutic drugs act primarily on replicating cells, with non-replicating cells being much less sensitive. Antibodies are well suited for this application since delivery is more readily achieved to highly accessible marrow versus normal organs and solid tumors. In addition, an anti-receptor or growth blocking antibody, possessing the ability to modulate a receptor or binding sites, could differentially effect lymphoid versus epithelial tissues. Decreasing the sensitivity of progenitors to toxic drugs would increase the bone marrow reserves and enhance subsequent response to colony stimulating factors, and enable higher doses of chemotherapy or reduce the interval to reconstitution. It should also be recognized that such positive effects on bone marrow progenitors, as a natural consequence of vitamin $B_{12}$ receptor therapy for cancer, is an additional mechanism by which the therapeutic index of chemotherapeutic drugs other than 5-FU and methotrexate can be improved.

In a variety of autoimmune diseases, graft versus host disease, ectopic allergy, and organ transplantation, an initial "induction" phase, in which the patient becomes sensitized to self or allo-antigens, is followed by a "proliferative" phase in which forbidden or unregulated clones of B- or T-cells are expanded. It has long been known that treatment with anti-proliferative, chemotherapeutic drugs following induction can inhibit expansion of forbidden clones, inhibit progression of disease, and restore a stable state of tolerance. An antibody, OKT-3, that controls the proliferation of allo-antigen-sensitized T-cells, has been approved for management of acute allograft rejection. Anti-receptor or growth blocking antibodies of the present invention can be substituted for extremely toxic chemotherapeutic drugs or highly immunogenic antibodies such as OKT-3 and achieve a similar state of tolerance without these associated drawbacks.

Inflammation is an application for which these agents are already being utilized in clinical trials. The primary emphasis has been on inhibiting the early manifestations of inflammation by inhibiting recruitment or binding of inflammatory cells to vascular endothelium of injured tissue. It also well recognized that proliferation of cells at the site of inflammation contributes to the pathology and tissue destruction of both acute as well as chronic inflammation. To this end, anti-proliferative, chemotherapeutic drugs have been widely used to inhibit sequelae of inflammation.

Methotrexate is one such drug commonly used to treat symptoms associated with rheumatoid arthritis. The drug acts to reduce both localized (e.g., synovium) and generalized inflammation associated with disease progression. Methotrexate acts synergistically with vitamin $B_{12}$ depletion in therapy of leukemia. Vitamin $B_{12}$ antagonists can therefore be combined with methotrexate to enhance efficacy in rheumatoid arthritis. Other methotrexate applications include treating destructive inflammation associated with chronic heart disease and colitis.

Surgery, radiation or chemotherapy to the abdomen is often complicated by the development of tissue adhesions. These represent a considerable clinical problem because they lead to bowel blockage and require surgical intervention. Peritoneal adhesions arise as a result of proliferation of the cells of the peritoneal membrane lining the abdomen. A non-toxic means of interfering with such proliferation could lead to restoration of these normal cells to homeostatic control mechanisms and thereby inhibition of adhesion formation. A similar process of benign proliferation and subsequent scarring is a complication of retinal surgery. Direct instillation of a small molecule analog of an antibody receptor antagonist could prevent such disabling complications.

Growth blocking or anti-receptor agents of the present invention are administered in a therapeutically effective dose which may be determined by in vitro experiments followed by in vivo studies. A therapeutically effective dose of growth blocking or anti-receptor agent and the timing of administration are determined by any means known in the art, including by measuring serum concentrations. For example, antibody administered in a dose range of 1 to 500 mg is quantitated in serum by solid phase, competition ELISA using biotinylated growth blocking agent binding to a solid-phase binding site source (e.g., purified, serum, TcII or recombinant TcII.) Unlabeled antibody is used as a competitor to develop a standard curve while growth blocking agents in serum aliquots is quantitated. As shown in FIG. 2, the serum half-life of a typical immune complex of IgG antibody is 24 hours, requiring dosing approximately every 36 to 48 hours to maintain serum concentrations above that required for maximal blockade (shown by tri-partite line). The longer the inherent serum half-life of the growth blocking or anti-receptor agent, the fewer administrations required. Thus, an immune complex IgM antibody with a half-life of several days may be more advantageous under certain circumstances.

The term "treatment" as used within the context of the present invention, refers to reducing or alleviating symptoms in a subject, preventing symptoms from worsening or progressing, inhibition or elimination of the causative agent, or prevention of the infection or disorder in a subject who is free therefrom. Thus, for example, treatment of infection includes destruction of the infecting agent, inhibition of or interference with its growth or maturation, neutralization of its pathological effects and the like. A disorder is "treated" by partially or wholly remedying the deficiency which causes the deficiency or which makes it more severe. An unbalanced state disorder is "treated" by partially or wholly remedying the imbalance which causes the disorder or which makes it more severe.

Pharmaceutical compositions containing the growth blocking or anti-receptor agents in an admixture with a pharmaceutical carrier or diluent can be prepared according to conventional pharmaceutical compounding techniques. The carrier may take a wide variety of forms depending on the form of preparation desired for administration, e.g., intravenous, oral topical, aerosol, suppository, parenteral or spinal injection.

The following examples are designed to illustrate the production and use of certain anti-receptor and growth blocking agents. The type of anti-receptor agent used in the examples is a human or chimeric antibody applied to the treatment of AIDS Related Lymphoma (ARL), a particularly aggressive form of cancer arising in AIDS patients, as well as other medical applications. Small molecule and peptide analogs may also be used for treatment of cancer, but are more optimally used in other pharmaceutical applications. The following examples are offered by way of illustration and not by way of limitation.

EXAMPLES

Example 1

Identification and Characterization of Functional Monoclonal Antibodies to the Vitamin $B_{12}$ Receptor Hybridomas are generated by PEG mediated fusion of murine splenocytes from mice, immunized as shown in FIG. 1, and HGPRT-myeloma cells like NS-1. For immunogens, transcobalamin II, present in Cohn-purified serum protein, is covalently immobilized (CnBr Sepharose) and used to adsorb small quantities of solubilized receptor. The complex is then used to immunize mice. Four to six weeks after fusion, hybridoma supernatants are screened in a functional assay for inhibition of vitamin $B_{12}$ uptake in K562 leukemic cells cultured in chemically defined medium using a modified radio labeled assay with 57 Co-vitamin $B_{12}$ complexed with transcobalamin II from Cohn fractions. The results of the primary screen in microtiter plates are illustrated in Table 4 below and expressed as the fraction of the uninhibited control (well A1). Well H12 serves as the positive control (maximum inhibition) and utilizes serum as a source of unlabeled vitamin $B_{12}$ complexed to transcobalamin II as competitor.

TABLE 4

Primary Screen of Hybridomas

| | 1 | 2 | 3 | 4 | 5 | 6 | 7 | 8 | 9 | 10 | 11 | 12 |
|---|---|---|---|---|---|---|---|---|---|---|---|---|
| A | 1.000 | .986 | .995 | .973 | .322 | .898 | .994 | .993 | .982 | .988 | .987 | 1.000 |
| B | .788 | .922 | .888 | .965 | .986 | .923 | .898 | .993 | .942 | .986 | .897 | .954 |
| C | .972 | >1.000 | .984 | .832 | .964 | .777 | .885 | .924 | .987 | .845 | .892 | 1.000 |
| D | .983 | .111 | .986 | .799 | .912 | .943 | 1.000 | .956 | .964 | .955 | .913 | .987 |
| E | .788 | .922 | .888 | .965 | .986 | .923 | .898 | .993 | .942 | .986 | .897 | .954 |
| F | 1.000 | .986 | .995 | .973 | .988 | .898 | .994 | .993 | .982 | .198 | .987 | 1.000 |

TABLE 4-continued

Primary Screen of Hybridomas

|   | 1 | 2 | 3 | 4 | 5 | 6 | 7 | 8 | 9 | 10 | 11 | 12 |
|---|---|---|---|---|---|---|---|---|---|----|----|----|
| G | .983 | .986 | .986 | .799 | .912 | .943 | 1.000 | .956 | .964 | .955 | .913 | .987 |
| H | .972 | 1.000 | .984 | .832 | .964 | .777 | .885 | .924 | .987 | .845 | .892 | .089 |

The hybridomas identified in this primary screen (A5, C2, D2, and F10) are cloned by limiting dilution with thymic feeder cells. Four to six weeks later, clones (identified by sequential numbering) from the primary wells are rescreened in the functional assay to identify those clones retaining the characteristic activity of the parents. In addition other assays are performed to characterize the specificity of the clones by inhibition of vitamin $B_{12}$ uptake on carcinoma versus leukemia cells or normal, mitogen stimulated lymphocytes. The results of the assessment of specificity are shown in Table 5 below.

TABLE 5

Assessment of Specificity

| Clone | Target Cells | | |
|---|---|---|---|
| Lymphocytes | Carcinoma | Leukemia | Normal |
| A5/8  | .386 | .333  | .287 |
| A5/12 | .342 | .384  | .317 |
| C2/2  | .989 | >1.000 | >1.000 |
| C2/5  | .923 | >1.000 | >1.000 |
| D2/20 | .656 | .089  | .154 |
| D2/7  | .891 | .174  | .245 |
| F10/4 | .198 | .123  | .423 |
| F10/8 | .234 | .312  | .666 |

Based upon these results the antibody D2/20 is selected for further evaluation in treatment of lymphoma. The antibody is able to strongly inhibit vitamin $B_{12}$ uptake at levels of antibody as low as 10 nanograms/ml (not shown). In addition, the antibody appears to inhibit uptake of vitamin $B_{12}$ in lymphoid cells but not those of epithelial origin, a characteristic which is potentially useful in decreasing toxicity to replicating crypt cells in colonic epithelium. In other assessments, the antibody did not inhibit uptake of vitamin $B_{12}$ in mitogen stimulated murine splenocytes, indicating its specificity for the human receptor.

Example 2

In Vitro Assessment of Cell Killing Potential of Vitamin $B_{12}$ Anti-Receptor Antibody Alone and in Combination with Chemotherapeutic Drugs Antibody D2/20 at a range of concentrations is incubated with Raji Burkitt lymphoma cells in microtiter plates for three days with and without chemotherapeutic drugs. Cell viability is measured by reduction of tetrazolium dye. Only viable cells metabolize the dye to an insoluble, colored product which is subsequently solubilized and read in a spectrophotometer. The results of the assay are shown in Table 6 below.

TABLE 6

| 100 | 10 | 1 | 0 | |
|---|---|---|---|---|
| | | Antibody (nanograms/ml) | | |
| .268 | .435 | .723 | .987 | 0 |
| .055 | .077 | .212 | .993 | 0.1 |
| | | Methotrexate (micrograms/ml) | | |
| .048 | .052 | .089 | .798 | 1 |
| .047 | .048 | .054 | .563 | 10 |

100% lysis control = .047

Based on these results, the antibody to the vitamin $B_{12}$ receptor is able to elicit cell death of the lymphoma cells, presumably by starving them of vitamin $B_{12}$. In addition, when combined with methotrexate, the combination appears to be synergistic since it was considerably more active than either of the two agents alone. The results are consistent with those obtained with other methods of vitamin $B_{12}$ depletion.

Example 3

In Vivo Assessment of Vitamin $B_{12}$ Anti-Receptor Antibody in Combination with Chemotherapeutic Drug Nu/nu mice are injected subcutaneously with 1 million Raji Burkitt lymphoma cells. After two weeks, barely palpable nodules are present at the injection site. Measurements are made in three dimensions with a planarimeter and equally sized tumors assigned to experimental groups of 10 mice. Mice are injected intravenously with the drug, methotrexate (3 dose levels-50, 10, and 5 Milligrams/$M^2$) and antibody D2/20 at 100 micrograms/mouse. Therapy is administered once weekly. Controls of antibody and drug alone, as well as vehicle controls, are included. Mice are monitored visually for toxicity, death, and tumor size weekly for 8 weeks, at which time the experiment is terminated, the mice sacrificed, and the tumors removed and weighed. The average of serial tumor measurements converted to weight (grams) is shown in Table 7 below.

TABLE 7

| | Week | | | | | | | |
|---|---|---|---|---|---|---|---|---|
| Group | 1 | 2 | 3 | 4 | 5 | 6 | 7 | 8 |
| Vehicle | .05 | .12 | .34 | .67 | 1.3 | 2.9 | 6.0 | — |
| Antibody (Ab) | .06 | .09 | .12 | .22 | .35 | .57 | .83 | 1.02 |
| Drug (50) | .04 | .10 | .25 | .41 | .73 | 1.4 | 2.3 | 3.4 |
| Drug (10) | .05 | .12 | .30 | .53 | .92 | 2.1 | 4.8 | 6.9 |
| Drug (5) | .07 | .14 | .43 | .70 | 1.2 | 2.6 | 4.8 | 7.2 |
| Ab + Drug (50) | .05 | .07 | .11 | .09 | N.D. | N.D | N.D. | N.D. |

TABLE 7-continued

| Group | Week | | | | | | | |
|---|---|---|---|---|---|---|---|---|
| | 1 | 2 | 3 | 4 | 5 | 6 | 7 | 8 |
| Ab + Drug (10) | .06 | .08 | .13 | .15 | .12 | .07 | N.D. | N.D. |
| Ab + Drug (5) | .05 | .07 | .11 | .21 | .24 | .17 | .15 | .11 |

— = Not measurable due to tumor necrosis
N.D. = Not detectable

Based upon these results, it can be concluded that vitamin $B_{12}$ anti-receptor antibody is active in inhibiting tumor growth in this model of human Burkitt lymphoma, and that its combination with methotrexate provides a more effective regimen.

Example 4

Treatment of a Patient with AIDS Related Lymphoma with Vitamin $B_{12}$ Anti-Receptor Antibody in Combination with Chemotherapy A patient diagnosed with AIDS Related Lymphoma ("ARL") is admitted to the hospital for treatment. The patient presents with CNS involvement and poor prognosis and is suffering from a fever of unknown origin. The patient has CD-4 counts below 200/μl and has been receiving anti-retroviral therapy, AZT (zidovudine), prior to diagnosis of ARL. The patient is given an aggressive regimen combining chemotherapy with bone marrow support (rGM-CSF) according to the following protocol:
A. Cyclophosphamide, 200 mg/$M^2$, IV over 30 minutes daily on days 1 through 5;
B. Vincristine 1.4 mg/$M^2$ IV push on day 1, not to exceed 2 mg/dose;
C. High dose methotrexate, 1500 mg/$M^2$ day 1, 150 mg/$M^2$ administered over 30 minutes with the subsequent 1350 mg/$M^2$ administered over the next 23½ hours, rapid urine flow maintained with the urine pH's supplemented with sodium bicarbonate to maintain the urine pH >7.5;
D. Folinic acid, 30 mg IV or orally administered every six hours (q6h), beginning 12 hours after the completion of the methotrexate infusion, folinic acid is continued until the serum methotrexate level is 0.01 uM;
E. Mitoxanthrone, 10 mg/$M^2$ IV push on days 4 and 5;
F. Decadron, 5 mg/$M^2$ IV push on days 4 and 5;
G. rGM-CSF, 3 μg/kg subcutaneously twice a day (bid), through day 6, until the absolute granulocyte count is >1,000/ul; and
H. Cytarabine (50 mg) intrathecal on day 1 of course 1; thereafter intrathecal methotrexate (12 mg) on day 1 and intrathecal cytarabine on day 16 for each of six other courses of therapy.

The patient is also administered antibiotics and Diflucan prophylactically. AZT is discontinued during chemotherapy. The patient receives seven courses of therapy and is assessed to have experienced a partial response of nodal disease and a complete response of CNS disease. After 7 months the patient returns to the hospital with relapsing disease peripherally, but still negative for CNS involvement.

The patient is treated with the same combination regimen with the following exceptions: RGM-CSF is not included due to concerns for accelerating tumor growth, no intrathecal treatment, and the inclusion of vitamin $B_{12}$ receptor antibody. In particular, antibody is administered on day 1 of each course of chemotherapy. The antibody component of the regimen consists of a "humanized" chimeric IgM derived from the murine antibody D2/20, administered at a dose of 100 mg in a IV drip over 4 hours. The antibody has been previously determined to have a serum half-life of 72 hours in patients.

The patient is removed from treatment after only three courses due to a non-responding neutophil count due to the lack of rGM-CSF. After 4 months however, the patient is assessed to have experienced a complete response of peripheral disease. The patient continues in complete response for 17 months.

Example 5

Figure 3:
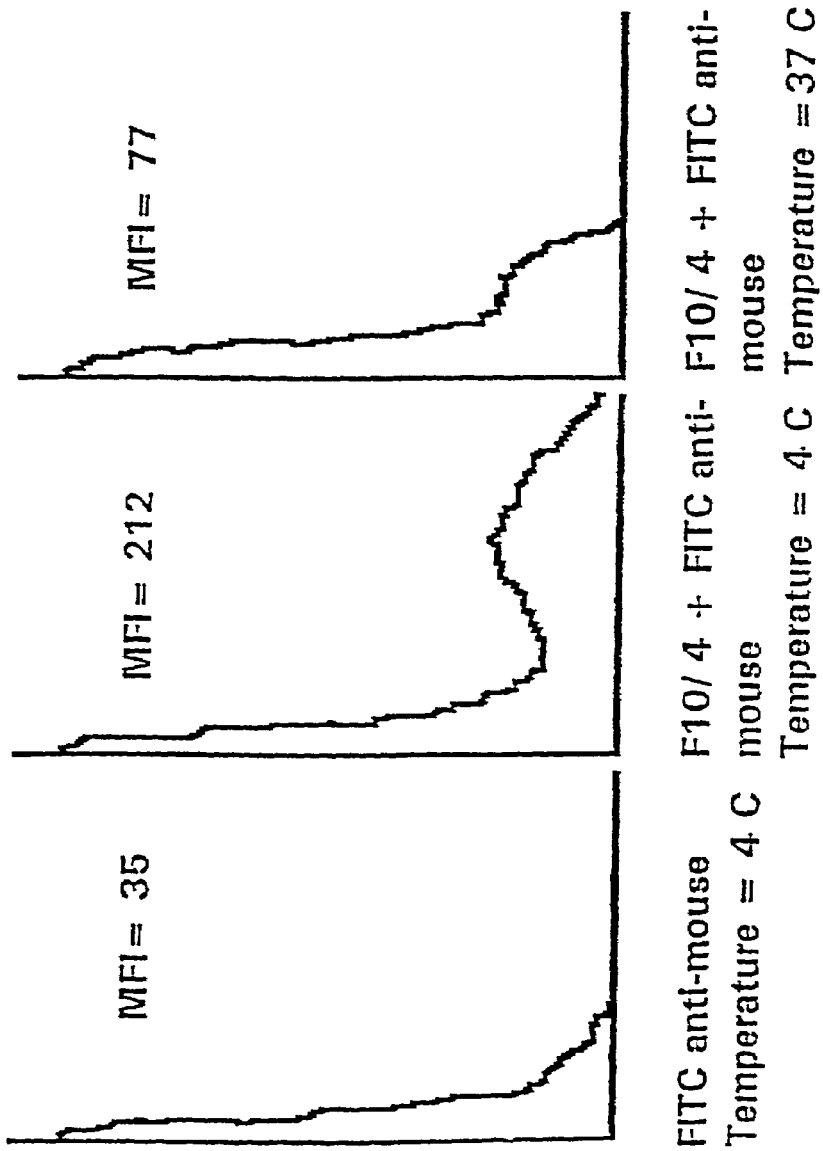
FIG. 3 illustrates assessment of vitamin $B_{12}$/transcobalamin II receptor modulation by vitamin $B_{12}$ anti-receptor antibodies. 100 ng/ml of antibody is incubated with 1 million Raji Burkitt lymphoma cells. Half of the cells are held at 4.0° C. and half transferred to 37° C. after washing. Thirty minutes to 2 hours later, samples are assessed for residual mouse Ig bound to cells by flow cytometry (MFI=mean fluorescence intensity) of all cells.

Identification of Monoclonal Antibodies Capable of Vitamin $B_{12}$ Receptor Modulation The hybridomas positive in the assay for inhibition of Vitamin $B_{12}$ uptake (Example 1 above) are screened in a different assay designed to identify those hybridomas capable of receptor modulation. Hybridoma supernatants are incubated with $1 \times 10^6$ K562 leukemic cells at 4° C. for 60 minutes. Cells are resuspended, washed and an equal aliquot of cells ($5 \times 10^5$) removed to a separate tube and incubated at 37° C. for 60 minutes while the other aliquot is retained at 4° C. for the same period. Both aliquots from each hybridoma are analyzed for bound mouse immunoglobulin by staining with fluorescein isothiocyanate-conjugated, anti-mouse immunoglobulin (FITC-αMIg). Unbound, secondary antibody is removed by washing, and stained cells examined using a Coulter Epics C flow cytometer. The mean fluorescent intensity (MFI) of positive cells and the binding profile are compared on the two aliquots of cells. Of the antibodies identified in Example 1, only the sister clones F 10/4 and F 10/8 are positive for receptor modulation as shown in FIG. 3. Fluorescence intensity of the sample held at 37° C. is significantly lower than the one held at 4° C., and constitutes preliminary evidence of receptor modulation.

Parameters for receptor modulation or "capping" are further detailed by studies with microtubule and microfilament inhibitors like colchine or vinblastine, to demonstrate the requirement of cytoskeleton in modulation. Studies are also performed with sodium oxide to demonstrate the dependence of capping on cellular energy processes. In addition, the time to complete expression of receptors is determined to be 24 hours, and it is determined that only nanogram/ml levels of antibody are required to maintain cells devoid of receptors which results in complete inhibition of thymidine uptake within 72 hours.

Example 6

Treatment of a Patient with Graft Versus Host Disease (GVHD) with Vitamin $B_{12}$ Anti-Receptor Antibody An adult patient with acute leukemia enters the hospital for an induction regimen prior to bone marrow transplantation. The patient receives cytosine arabinoside, 3 g/$M^2$, every 12 hours for 6 days, followed by fractionated total body irradiation, 200 cGy, twice daily for 3 days. The patient is administered T-cell depleted, histocompatible marrow following induction, along with cyclosporine and methotrexate for prophylaxis of GVHD. The cyclosporine is administered through a silastic catheter from day 1 through day 180 at a dose level of 1.5 mg/Kg/d for the first 15 days, followed thereafter at a dose level of 3 mg/Kg/d. Methotrexate is administered at a dose of 0.25 mg/Kg/d on days 1, 3, 6, 11, 18, 25, and 31.

The patient demonstrates engraftment and has no evidence of GVHD up to 3 months. At that time, however, the patient is readmitted to the hospital and diagnosed as suffering from Grade III GVHD while still receiving cyclosporine A. The patient is once again administered methotrexate but in combination with Vitamin $B_{12}$ anti-receptor antibody. The regimen consists of administration of a "humanized" chimeric IgM derived from the murine antibody F10/4 at a dose of 50 mg in an IV drip over 4 hours followed by methotrexate infusion (0.25 mg/Kg/d). The regimen is administered on days 1, 3, 6, and 11 while maintaining cyclosporine administration. After two weeks most manifestations of GVHD have resolved and the patient is maintained on cyclosporine for an additional 60 days. The patient remains free of GVHD for two years at which time he relapses from leukemia and dies.

Example 7

Reduction in Hematologic Toxicity of Chemotherapeutic Drugs with Vitamin $B_{12}$ Anti-Receptor Antibody A patient with stage 1V colon cancer with both lymph node and liver involvement is admitted to the hospital for treatment. The patient is administered a regimen of leucovorin (200 mg/$M^2$), given as a 10-minute infusion, followed by a dose of 1,000/$M^2$ of 5-fluorouracil every two weeks. Therapy is stopped after 2 months due to grade III/IV leukopenia and thrombocytopenia. The patient experiences a partial response of liver and lymph node disease and only minimal neurotoxicity.

The patient is re-treated by prior infusion of an IgM, "humanized" chimera of antibody F10/4, capable of modulating the vitamin $B_{12}$ receptor. The patient is infused with 2 mg of antibody over 2 hours, a dose found previously to modulate the receptor on bone marrow cells, but which is virtually undetectable by immunoperoxidase in biopsies of solid tumor lesions of patients. After 18 hours the patient is infused with 5-fluorouracil and leucovorin as before. The patient continues receiving treatment every 2 weeks for 4 months and experiences only Grade 1 thrombocytopenia and moderate neurotoxicity. After this second treatment interval, the patient is assessed to have experienced a complete response of lymph node disease with a virtual complete response of liver disease.

Example 8

Production of Recombinant TcII

Preparation of the TcII cDNA. The full-length cDNA for TcII that was previously isolated from a human endothelial cell cDNA library in λ gt II and subcloned into PGEM 3Z f(−) vector (Platica, O. et al., *J. Biol. Chem* 266:7860, 1991) was amplified in liquid culture and isolated by alkaline lysis and cesium chloride gradient centrifugation. (Sambrook J. et al., "Molecular Cloning, A Laboratory Manual" Cold Spring Harbor Laboratory Press, 1989.) The plasmid was digested with EcoRI and the cDNA insert was separated by electrophoresis in 0.8% low melting point (LMP) agarose gel, and recovered from the agarose by phenol extraction followed by ethanol precipitation. (Sambrook J. et al., "Molecular Cloning, A laboratory Manual, Cold Spring Harbor, N.Y.," Cold Spring Harbor Laboratory Press, 1989.)

Insertion of the cDNA into a plasmid vector for baculovirus. The plasmid, PVL 1393, (Webb, N. R. et al., *Technique* 2:173, 1990), was amplified in *Escherichia coli* JM 109 and purified by cesium chloride gradient centrifugation. (Sambrook J. et al., "Molecular Cloning, A Laboratory Manual," Cold Spring Harbor Laboratory Press, 1989.) To insert the TcII cDNA into this vector, the plasmid was linearized by EcoRI digestion and isolated from LMP agarose following electrophoresis. The full-length TcII cDNA (1866 bp) encompassing a 54-nucleotide (nt) leader peptide, a 37-nt 5' untranslated region, and a 548-nt 3' untranslated region, including the polyadenylation signal, was inserted into this plasmid, and clones containing the cDNA in the correct orientation for the translation of the protein were identified by the predicted size of the fragments following digestion of the insert containing plasmid with restriction enzymes.

Culture of SF9 cells. SF9 cells (ATCC 1711-CRL) were propagated at 27° C. in TNM-FH medium (Sigma Chemical Co, St. Louis, Mo.) and supplemented with 10% heat inactivated fetal bovine serum (FBS) (GIBCO, Grand Island, N.Y.) as described by Summers and Smith. (Summers, M. et al., *Texas Agricultural Experiment Station Bulletin No.* 1555, College Station, Tex., Texas A&M University, 1987.)

Isolation of the wildtype baculovirus. SF9 cells were infected with *Autographa californica* nuclear polyhedrosis virus (AcNPV) at a multiplicity of infection (MOI) of 10. Following incubation at 27° C. for 72 hours, the medium was collected, and the extracellular virus in the medium was collected, and the extracellular virus in the medium was purified by sucrose density gradient centrifugation.

Generation and isolation of recombinant virus. The production and isolation of recombinant virus was performed as described by Summers and Smith (Summers, M. et al., *Texas Agricultural Experiment Station Bulletin No.* 1555, College Station, Tex., Texas A&M University, 1987), using the calcium phosphate transfection protocol. (Graham, F L et al., *Virology* 52:456, 1973.) The recombinant virus in the 96-hour post-transfection medium was purified by plaque assay in LMP agarose plates. Recombinant plaques were identified by visual screening and confirmed by dot-blot hybridization of DNA from infected SF9 cells using the TcII cDNA as the probe. All subsequent assays for the recombinant virus were performed by measuring the binding of [$^{57}$Co]$B_{12}$ (Amersham, Arlington Heights, Ill.) to recombinant TcII in the postculture medium of SF9 cells infected with virus recovered from individual plaques. The recombinant TcII produced in the bacculovirus, has the same functional properties as native human TcII. The production of this protein and its properties is described in detail in Quadros, *Blood,* 81:1239, 1993.

Purification of recombinant TcII. The culture medium from SF9 cells infected with recombinant virus for 100 to 120 hours was collected, and the cell debris was removed by centrifugation at 3,000 g for 15 minutes. The recombinant TcII was purified by affinity chromatography using the photolabile $B_{12}$-Propyl-Sephacryl (Pharmacia LKB) as described previously in Quadros, E. V. et al., *J. Biol. Chem* 261:15455, 1986, with the following modification: for the batchwise purification of TcII, 2 g CM-Sephadex C-50 (Pharmacia LKB) was added to each liter of culture medium, which had been titrated to pH 5.2 with 1N HCl. The final step of the purification procedure as previously described, (Quadros, E. V. et. al., *J. Biol. Chem* 261:15455, 1986), was omitted, because the protein released from the affinity matrix was devoid of any contaminating proteins as determined by sodium dodecyl sulfate-polyacrylamide gel electrophoresis (SDS-PAGE).

Example 9

Production of Antibodies to TcII

Murine monoclonal antibodies were produced by conventional methods from immunized animals using recombinant human TcII produced in Example 8. The hybridomas were cultured and plated. Wells demonstrating hybridoma growth were screened for the presence of antibodies against TcII by the enzyme linked immunoabsorbent assay ("ELISA") as described in Hermanson et al., *Immobilized Affinity Ligand Techniques*, Academic Press, 1992. Positive wells were identified and then tested for presence of antibodies against apo-TcII (FIG. 4, type 1) by measuring their ability to inhibit binding of $^{57}$Co labeled vitamin $B_{12}$ to TcII in a radioimmunoassay (RIA). TcII is coated onto microtiter plates. Radiolabeled vitamin $B_{12}$ and the antibody sample are incubated on the plate for three (3) hours at 37° C. After decanting the mixture and washing the microtiter plate with PBS X3, the radioactivity of the plate is measured. The results are reported as percentage inhibition in FIG. 5.

Example 10

Assay for Cellular Uptake of holo-TcII used to Isolate Monoclonal Antibodies which Inhibit Cellular Uptake of Vitamin $B_{12}$ The ELISA data generated in Example 9 was then used to select hybrids to test for ability to inhibit uptake of the labeled vitamin $B_{12}$ in a biological preparation. 1-18, 2-2, 3-4, 3-11, 3-16, 4-4, 4-7, 5-2, 5-12, 5-4, 5-19, 6-4, 6-13, 7-4, 8-4, and 5-18 were chosen on the basis of their performance as evaluated by the ELISA.

Human erythroleukemia cells K562 (ATCC accession number CCL 243) were used to evaluate vitamin $B_{12}$ uptake. They were typically cultured for 48 to 72 hours in RPMI 1640 medium containing 10% fetal bovine serum before use. Vitamin $B_{12}$ labelled with $^{57}$Co (Amersham, Arlington Heights, Ill. or Eastman Kodak, Rochester, N.Y.) in a volume of 100 uL was first bound to TcII in a volume of 500 uL by mixing and incubation at room temperature for 30 minutes. The TcII [$^{57}$Co]$B_{12}$ complex was then incubated with each monoclonal antibody to be tested (including 2-2, 4-7, 3-11) (in the form of culture supernatant or ascites), or with appropriate controls such as irrelevant culture supernatant (irrelevant ascites or mouse serum), at 4° C. overnight. The cells were harvested and washed twice in Hank's balanced salt solution (HBSS), at between 1 and 1.5×10$^6$ cells in 500 uL. These cells were added to the antibody/TcII[$^{57}$Co]$B_{12}$ mixture along with 100 uL of 10 nM calcium and incubated for 1 hour at 37° C. One hundred uL of 100 nM EDTA was used in place of calcium to determine non-specific binding since TcII binding to the receptor is calcium dependent. Cellular uptake of [$^{57}$Co]$B_{12}$ was determined by counting the radioactivity from $^{57}$Co in the cell pellets produced by centrifuging the samples at 2000 RPM for 5 minutes in a Hermle Centrifuge. These results are reported in FIG. 6. A surprising result was that several clones also increased uptake. This may be a result of the presence of TcII in the mouse ascites.

Example 11

Determination of Specificity for Holo- or Apo-TcII

Three of the clones which inhibited vitamin $B_{12}$ uptake (2-2, 3-11, 4-7) (FIG. 5), were then tested to determine their specificity for holo- versus apo-form of TcII using conventional immunoprecipitation techniques. Specifically, recombinant TcII purified by chromatography on carboxymethyl-Sephadex (Quadros et al., *J. biol. Chem.*, 261(33):15455-15460, 1986) to yield the apo-form of the carrier protein was radiolabeled with $^{125}$I (Amersham) as previously described in (Quadros et al., *Am. J. Physiol.* 256:296-303, 1989.) Holo-TcII was prepared from this material by incubating an aliquot at room temperature for 30 minutes with sufficient vitamin $B_{12}$ (Sigma) to saturate apo-TcII. Antibodies to be tested were captured on Sepharose beads conjugated with protein-A, washed in HBSS, incubated with either $^{125}$I-holo-TcII or $^{125}$I-apo-TcII, washed, and bound radioactivity determined on a gamma counter. A polyclonal rabbit antibody to TcII was used as a positive control.

Figure 7:
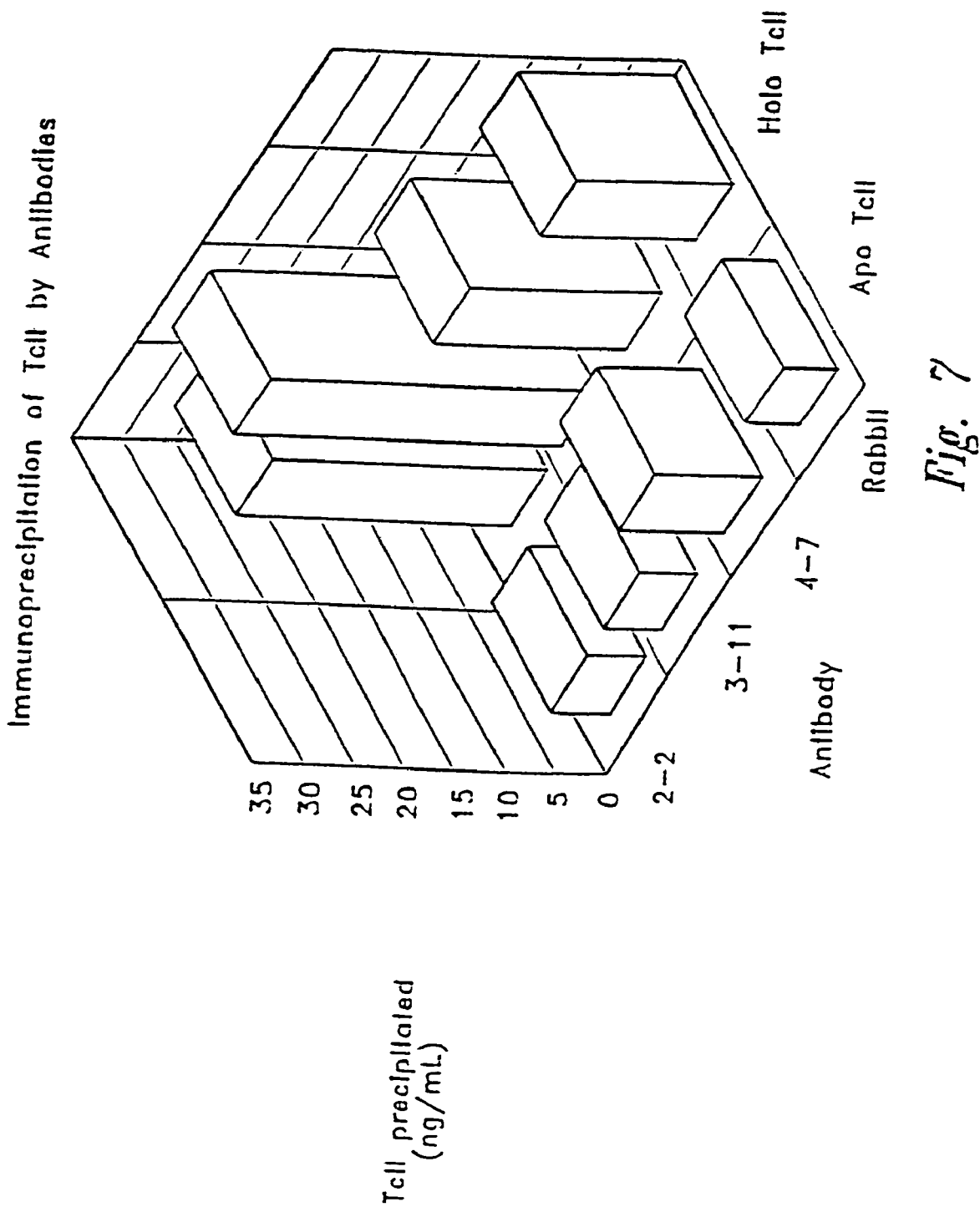
FIG. 7 illustrates the selectivity of monoclonal for holo-TcII assessed by immunoprecipitation.

As shown in FIG. 7, all three clones bound preferentially to holo-TcII. The results indicate that binding of vitamin $B_{12}$ to TcII leads to expression of a neodeterminant on the molecule. This determinant is related to the region of TcII that is recognized by the receptor, and that it may be responsible for the specificity of the receptor for holo-TcII.

Example 12

Purification of Antibodies

Growth blocking agents were produced by hybridoma clones 1-9, 3-9, 5-18, and 3-11 grown in DMEM 10% fetal bovine serum, 0.2% β-mercaptoethanol, and 2% 3T3 conditioned medium (a source of Interleukin 6) in 1 L glass roller bottles. The culture supernatant was collected and stored frozen prior to the commencement of this project. Thawed supernatant was filtered through a 0.22 μm filter to remove any bacteria or cell debris, then buffered with 1 M Hepes, pH 7.2. Antibody was purified from this culture medium by affinity chromatography on sheep-anti-mouse immunoglobulin columns as follows:

Column and buffers were allowed to warm to room temperature. Phosphate-buffered saline (1×PBS) with 0.5% sodium azide was allowed to drain from the column. The column was pre-cycled with 200 mL PBS, then 200 mL 0.1M glycine, pH 2.5, to clear any contaminants, then re-equilibrated with 200 mL of PBS. The pH of the buffer running through the column at this point was checked with pH paper to be 7.0-8.0. 200 mL of culture medium was applied to the column, allowed to run through and collected as "drop thru". This drop thru was then reapplied to the column. The pH was checked at this stage to be approximately 7.4. 200 mL PBS was added to the column to wash through any unbound protein, and the first 20 mL was collected in a separate tube as "wash 1". The pH was checked here to be 7.0-8.0. The last of the buffer was aspirated through the column with a syringe. 8 mL of 0.1 M glycine was added to the column and allowed to sit for 10 minutes. Eight 1 mL fractions were collected from the column, the pH was checked to be 2.5. The fractions were then neutralized with 35 μL of saturated tris buffer. Optical density readings of the elutes were taken at 280 nm to determine which ones had sufficient antibody to keep. Protein concentration was calculated in mg/mL using the equation:

$$1.4 \text{ O.D.} = 1 \text{ mg/mL.}$$

Elutes which gave O.D. readings above 0.12 were pooled and concentrated by high pressure filtration using a YM 10 43 mm membrane filter. PBS was washed through the filtration apparatus 3× to wash out any glycine/tris buffer and to resuspend the antibodies in a solution of neutral pH. Optical density readings at 280 nm were taken to obtain the final concentration. The solutions were filtered sterile with a 0.22 μm syringe filter and stored at 4° C.

Example 13

Determination of Purified Protein as Antibody

The purified protein samples were determined to be antibody by electrophoresis on SDS-PAGE gel, under both reducing and non-reducing conditions (to visualize both the entire antibody molecules and the heavy and light chains). SDS-PAGE mini-gels were prepared using Mini-PROTEAN II Dual Slab Cell from Bio-Rad Laboratories. Glass plates, spacers, combs, and casting stand gasket were cleaned with ethanol before use. The following procedure was used:

Gel sandwich was assembled ensuring that the plates and spacers were flush. A 6% acrylamide separating gel was prepared with 2 mL acrylamide, 5.44 mL distilled water, 2.5 mL 1.5 M Tris-HCl, pH 8.8, 50 μL 10% APS and 10 μL Temed. 4.7 mL was pipetted between two of the gel plates. A 12% gel was prepared similarly, with the exception that 4 mL of acrylamide and 3.44 mL of distilled water were used. To ensure that no air bubbles formed, a layer of distilled water was pipetted above each gel. Both gels were allowed to polymerize for 20 minutes. Distilled water was removed by vacuum.

Stacking gel was prepared with 0.833 mL acrylamide/Bis, 2.9 mL distilled water, 1.25 mL 1.5M Tris-HCl, pH 6.8, 20 μL 10% APS, and 10 μL of Temed. The gel was pipetted between the gel sandwiches and a comb was immediately placed into each and allowed to polymerize for 30 minutes. Combs were removed and the sample lanes rinsed with distilled water. Gels were attached to the inner cooling core and GST running buffer (Glycine, SDS, and Tris) was added to the center chamber.

Samples of the four monoclonal antibodies, 1-9, 3-9, 5-18, and 3-11 were prepared at 2-3 mg/mL, with bromophenol blue for the non-reducing 6% gel, and with both bromophenol blue and 2% β-Mercaptoethanol for the 12% reducing gel. These samples and both high and low molecular weight markers were loaded onto the gel, 5 μL was added per lane. The inner cooling core was placed into the lower buffer chamber. The chamber was filled with 1×GST, and any air bubbles were removed from the bottom of the gel.

The chamber was then sealed with the lid and connected to the power supply. The voltage was set at 100 volts until the samples reached the running buffer, when the voltage was raised to 200 volts. After electrophoresis was complete, the gel sandwich was removed from the apparatus. The upper and lower gel plates were detached and the stacking gel was discarded. The running gel was removed from the plate by placing the gel under 1× Semi-Dry Transfer buffer. The gels were fixed and stained using a modified from of the silver staining procedure of J. H. Morrissey (*Analytical Biochemistry*, 117: 307-310, 1981).

Example 14

Determination of Antibody Isotype

An ELISA sandwich assay was used to determine the isotype of each of the four monoclonal antibodies purified, as well as another potentially useful growth blocking antibody, 2-6. Antibody tested for 2-6 was not purified, culture supernatant was added directly to the ELISA wells.

100 μL of isotype-specific rat-anti-mouse capture antibody was added to each well of a flat-bottom 96 well Falcon polyvinyl ELISA plate at a concentration of 5 μg/mL (prepared in 1× PBS). Two rows were coated per isotype (IgG1, IgG2a, IgG2b, IgG3, IgM, kappa and lambda light chains). One row contained only PBS as a measure of the background signal. The ELISA plates were incubated at room temperature overnight in a sealed container lined with damp paper towels. The well contents were emptied by slapping the plates on a paper towel, and 100 μL of 1× PBS 0.5% milk powder was added to each well to block non-specific binding. This was incubated at room temperature for 1 hour.

The four purified monoclonal antibodies and the control antibody, 2E11, which is known to be IgG1 kappa, were prepared at 5 μg/mL in PBS/milk. The plates were washed three times in PBS/milk, then 100 μL of each antibody solution was added to each well of 2 columns of the ELISA plate, so that each antibody was tested against each isotype. This was incubated at room temperature for 1 hour. The wells were emptied and the plate washed as in step 3. 100 μL of rat-anti-mouse immunoglobulin which was labeled with horseradish peroxidase diluted 1:1000 in PBS/milk, was added to each well on the plate and incubated for 1 hour. The plate was again washed as in step 3 and then rinsed 3× with distilled water. 2,2' Azinobis (3-ethylbenzthiazoline sulfonic acid, or ABTS) substrate was prepared at 1 mg/mL in citrate buffer, pH 4.5, with 2 μL/mL freshly prepared 3% hydrogen peroxide. 100 μL of this solution was added to each well on the ELISA plate and allowed to stand at 37° C. for approximately 20 minutes. Once a color-change reaction was observed, the plate was read on Bio-Tek Microplate EL 309 ELISA Reader.

The isotypes of the purified antibodies are shown in Table 8.

TABLE 8

| | |
|---|---|
| 1-9 | IgG2a kappa |
| 3-9 | IgG1 kappa |
| 5-18 | IgG2a kappa |
| 2-6 | IgG1 kappa |
| 4-7 | IgG2b kappa |
| 2-2 | IgG2a kappa |
| 3-11 | 1gG2a kappa |

Example 15

Determination of Antibody Specificity for Transcobalamin II

Figure 8:
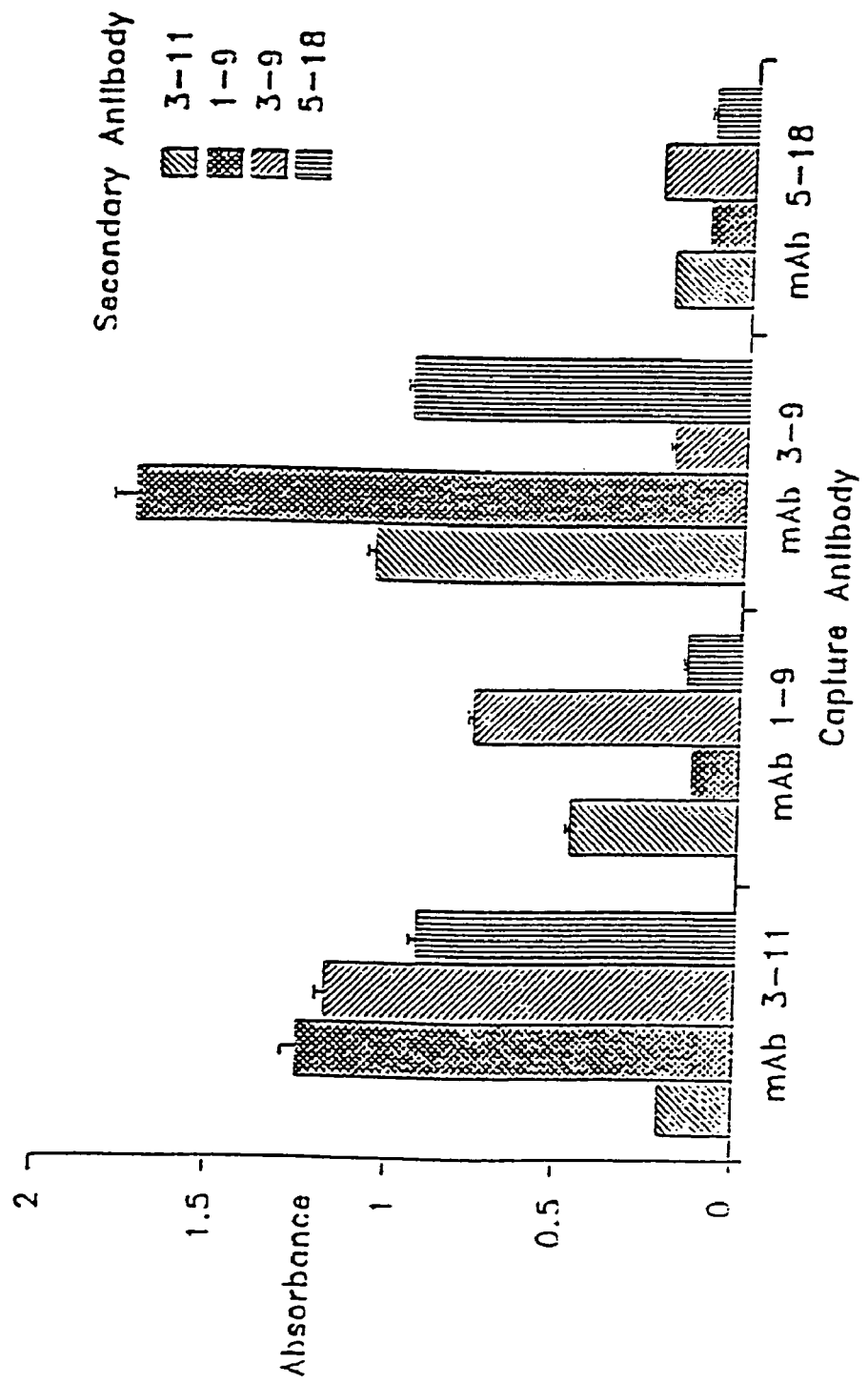
FIG. 8 illustrates a two-site ELISA assay for anti-TcII monoclonal antibodies. Transcobalamin II was detected in human serum with combinations of anti-TcII monoclonal antibodies. ELISA plates were coated with 10 ug/ml of monoclonal antibodies, 50 ul of human serum was added to blocked plates and bound TcII detected with biotinylated secondary monoclonal antibodies.

A similar ELISA sandwich assay was used to determine whether the purified antibodies recognize TcII as was used for the isotyping experiment. In this procedure, the four purified monoclonal antibodies were mixed together at 10 μg/mL (2.5 μg/mL of each antibody) in PBS and 100 μL was added to each well. This was incubated overnight, then the plates were washed and blocked in PBS 0.5% milk. 100 μL 5× concentrated human serum or 5× concentrated fetal bovine serum was added to the first well of each row on the plates. The sera were then titrated (serially diluted) in PBS/milk across the plates: each step diluted the sera 2×. This was incubated for 1 hour, washed and blocked, then purified anti-TcII antibodies which had been labeled with biotin were added, this time singularly, to each well of two rows. This was incubated for 1 hour, washed and blocked, then 50 μL of horseradish peroxidase-labeled streptavidin, diluted 1:2000 in PBS/milk, was added to each well. This was incubated for 2 hours, washed/blocked, substrate solution was added as per the isotyping protocol, and read on the ELISA reader. Once results were obtained from this experiment, it was repeated with normal concentration of human serum, mouse serum, rhesus monkey serum, and recombinant TcII. Mouse serum was of limited availability, so only 50 μL was added to the first well of ELISA plate instead of 100 μL. Results are shown in FIG. 8.

Antibody 5-18 was found to perform poorly as a capture antibody despite showing reasonable activity as a detector with 3-11 and 3-9. However, it showed no response in combination with 1-9, suggesting that both monoclonal antibodies may recognize the same epitope. The remaining combinations of monoclonal antibodies produced responses, which suggests that 3-11 and 3-9 see independent epitopes.

While the present invention has been disclosed and described with reference to specific embodiments, it will be understood by those skilled in the art that various changes or modifications in form and detail may be made without departing from the spirit and scope of this invention.

The invention claimed is:

1. A monoclonal antibody that binds to TcII, wherein said monoclonal antibody inhibits the binding of vitamin $B_{12}$ to TcII and inhibits cellular uptake of vitamin $B_{12}$.

2. A pharmaceutical composition comprising the monoclonal antibody of claim 1 and a pharmaceutically acceptable carrier or diluent.

3. A method of inhibiting cellular uptake of vitamin $B_{12}$ in a warm-blooded animal, comprising administering to a warm-blooded animal an effective amount of the monoclonal antibody of claim 1, such that vitamin $B_{12}$ cellular uptake is inhibited.

4. A method of inhibiting cellular uptake of vitamin $B_{12}$ in a biological preparation, comprising administering to a biological preparation an effective amount of the monoclonal antibody of claim 1, such that vitamin $B_{12}$ cellular uptake is inhibited.

5. A method of treating a neoplastic disorder in a warm-blooded animal, comprising administering to a warm-blooded animal an effective amount of the monoclonal antibody of claim 1.

* * * * *